(12) United States Patent
Allsworth et al.

(10) Patent No.: US 12,306,174 B2
(45) Date of Patent: May 20, 2025

(54) DIAGNOSIS OF CANCER

(71) Applicant: Owlstone Medical Limited, Cambridge (GB)

(72) Inventors: Max Allsworth, Cambridge (GB);
Edoardo Gaude, Cambridge (GB);
Marc van der Schee, Cambridge (GB)

(73) Assignee: Owlstone Medical Limited, Cambridge (GB)

( * ) Notice: Subject to any disclaimer, the term of this patent is extended or adjusted under 35 U.S.C. 154(b) by 891 days.

(21) Appl. No.: 17/273,294

(22) PCT Filed: Sep. 4, 2019

(86) PCT No.: PCT/GB2019/052468
§ 371 (c)(1),
(2) Date: Mar. 3, 2021

(87) PCT Pub. No.: WO2020/049300
PCT Pub. Date: Mar. 12, 2020

(65) Prior Publication Data
US 2021/0341461 A1 Nov. 4, 2021

(30) Foreign Application Priority Data
Sep. 4, 2018 (GB) ...................... 1814350

(51) Int. Cl.
*G01N 33/497* (2006.01)
*A61B 5/08* (2006.01)
(52) U.S. Cl.
CPC .......... *G01N 33/497* (2013.01); *A61B 5/082* (2013.01); *G01N 33/4975* (2024.05);
(Continued)

(58) Field of Classification Search
CPC ......... G01N 33/497; G01N 2033/4975; G01N 2430/00; G01N 2800/52;
(Continued)

(56) References Cited

U.S. PATENT DOCUMENTS 5,818,580 A * 10/1998 Murnick ................ G01N 21/73
356/311
2004/0077965 A1 4/2004 Hubbard et al.
(Continued)

FOREIGN PATENT DOCUMENTS

CN 2003215123 A 7/2003
CN 104650234 A 5/2015
(Continued)

OTHER PUBLICATIONS

Machado et. al. Detection of lung cancer by sensor array analyses of exhaled breath. Am J Respir Crit Care Med. Jun. 1, 2005;171(11):1286-91. doi: 10.1164/rccm.200409-1184OC. (Year: 2005).*

(Continued)

*Primary Examiner* — Thaddeus B Cox
*Assistant Examiner* — Karen E Toth
(74) *Attorney, Agent, or Firm* — Hamilton, Brook, Smith & Reynolds, P.C.

(57) ABSTRACT

A method for the early detection and monitoring of the progression of cancer by detecting breath biomarkers is provided. The method comprises assessing the activity of an aldo-keto reductase by measuring the concentration of an exogenous substrate for said enzyme and/or measuring the concentration of a metabolite of said substrate in exhaled breath of a subject. Preferably, the cancer is lung cancer.

22 Claims, 3 Drawing Sheets

Figure 1:
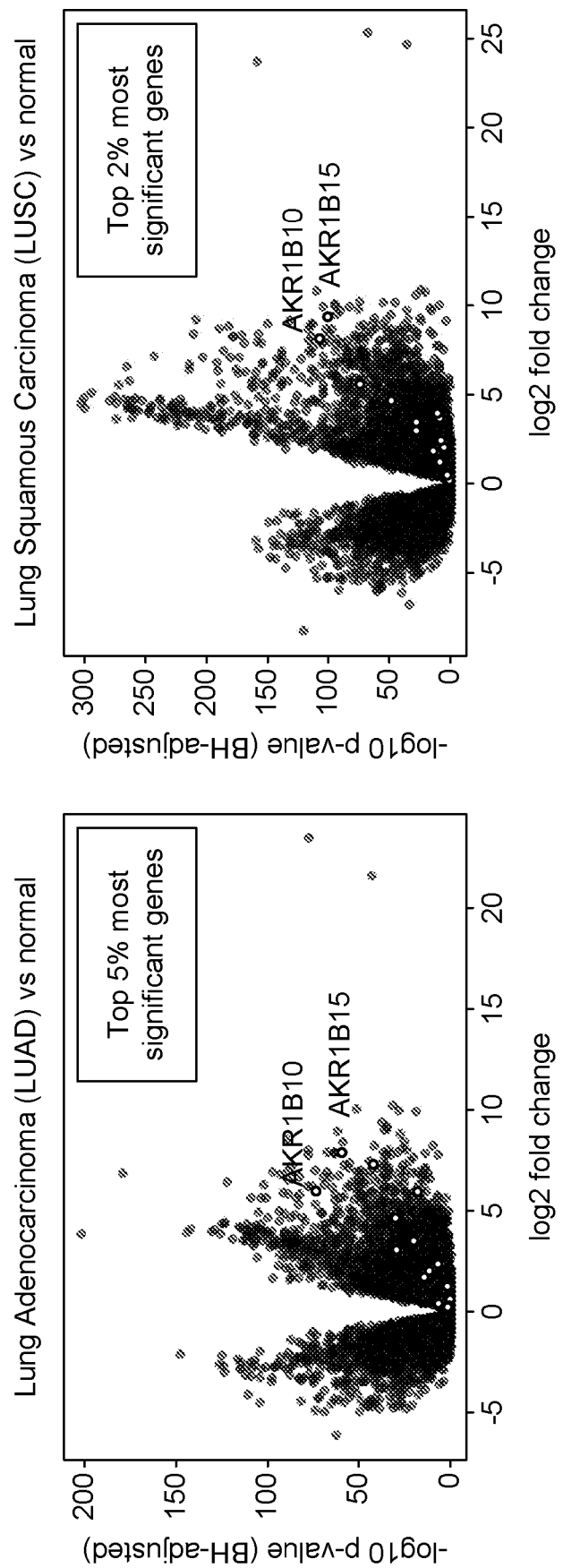

(52) U.S. Cl.
CPC ..... *G01N 2430/00* (2013.01); *G01N 2800/52* (2013.01); *G01N 2800/7028* (2013.01)

(58) Field of Classification Search
CPC ..... G01N 2800/7028; G01N 2333/904; G01N 33/57423; A61B 5/082; A61K 49/1815; A61K 51/1231; C12Q 1/26
See application file for complete search history.

(56) References Cited

U.S. PATENT DOCUMENTS

| | | | |
|---|---|---|---|
| 2004/0081587 A1* | 4/2004 | Melker | A61B 5/411 436/56 |
| 2005/0233459 A1 | 10/2005 | Melker et al. | |
| 2007/0172424 A1 | 7/2007 | Roser | |
| 2009/0005270 A1 | 1/2009 | Melker et al. | |
| 2010/0255598 A1 | 10/2010 | Melker et al. | |
| 2012/0115177 A1 | 5/2012 | Rodenrys | |
| 2012/0183949 A1* | 7/2012 | Hyde | B82Y 15/00 977/773 |
| 2015/0140676 A1 | 5/2015 | Dweik et al. | |
| 2016/0101194 A1 | 4/2016 | Dennis | |
| 2017/0303822 A1 | 10/2017 | Allsworth et al. | |
| 2017/0303823 A1 | 10/2017 | Allsworth et al. | |
| 2022/0228192 A1 | 7/2022 | Gaude et al. | |

FOREIGN PATENT DOCUMENTS

| | | |
|---|---|---|
| CN | 105 403 615 A | 3/2016 |
| JP | 3790792 B2 * | 6/2006 |
| JP | 2008-513026 A | 5/2008 |
| WO | 2006/034370 A2 | 3/2006 |
| WO | 2007/103474 A1 | 9/2007 |
| WO | 2008/134026 A1 | 11/2008 |
| WO | 2012/140660 A1 | 10/2012 |
| WO | 2013/040494 A1 | 3/2013 |
| WO | 2015/064063 A1 | 5/2015 |
| WO | 2017/187120 A1 | 11/2017 |
| WO | 2017/187141 A1 | 11/2017 |
| WO | 2018/009939 A1 | 1/2018 |
| WO | 2018/009939 A9 | 1/2018 |
| WO | 2018/211280 A1 | 11/2018 |
| WO | WO 2019/220145 A1 | 11/2019 |
| WO | 2020/049300 A1 | 3/2020 |

OTHER PUBLICATIONS

Machine Translation of JP3790792B2 (Year: 2003).*
In vitro analysis of volatile organic compounds in search of potential biomarkers of lung cancer; Kamila Schmidt, University of Salford Manchester, Aug. 2016 (Year: 2016).*
Nishinaka et al., "Identification and characterization of functional antioxidant response elements in the promoter of the aldo-keto reductase AKR1B10 gene", Chemico-Biological Interactions 276, 160-166 (2017).
Qiongfang, C., et al., "Expression and clinical significance of aldo-ketone reduction family 1B10 protein in non-small cell lung cancer" Theory and Practice of Diagnostics, vol. 11, No. 2, 2012, pp. 167-171.
Penning, T. M., et al., "AKR1B10: A New Diagnostic Marker of Non-Small Cell Lung Carcinoma in Smokers", Clin Cancer Res, vol. 11, No. 5, 2005, pp. 1687-1690.
International Preliminary Report on Patentability for International Application No. PCT/GB2019/051381, entitled Method to Evaluate Metabolic Activity of Liver Enzymes, consisting of 10 pages. Date Mailed: Nov. 17, 2020.
Alvarez, S.W. et al., "NFS1 undergoes positive selection in lung tumours and protects cells from ferroptosis," Nature, 551(7682): 639-643 (Nov. 2017).
Ayala, A. et al., "Lipid Peroxidation: Production, Metabolism, and Signaling Mechanisms of Malondialdehyde and 4-Hydroxy-2-Nonenal," Oxidative Medicine and Cellular Longevity, vol. 2014, Article ID 360438, Published May 8, 2014.
Bachur, N. 1976. "Cytoplasmic Aldo-Keto Reductases: A Class of Drug Metabolizing Enzymes." Science, 193 (4253): 595-597.
Barski, O.A. et al., "The Aldo-Keto Reductase Superfamily and Its Role in Drug Metabolism and Detoxification," Drug Metabolism Reviews, 40 (4): 553-624 (2008).
Blaser, M.J., Disappearing microbiota and epidemic obesity, Depts. of Medicine and Microbiology, New York University School of Medicine, Langone Medical Center, Dept. of Biology, NYU, 22 pages (2007).
Cao, D. et al., "Identification and Characterization of a Novel Human Aldose Reductase-like Gene," The Journal of Biological Chemistry, 273(19): 11429-11435 (1998).
Ciccarelli, F.D. et al., "Toward Automatic Reconstruction of a Highly Resolved Tree of Life," Science, 311: 1283-1287 (2006).
Costea, P.I. et al., "Towards standards for human fecal sample processing in metagenomic studies," Nature Biotechnology, 35: 1069-1076 (2017).
DeNicola, G.M. et al., "Oncogene-induced Nrf2 transcription promotes ROS detoxification and tumorigenesis," Nature, 475(7354): 106-109 (2012).
Dixon, S.J. et al., "Pharmacological inhibition of cystine-glutamate exchange induces endoplasmic reticulum stress and ferroptosis," eLife 3, 25 pages (2014).
Fan, T.WM. et al., "Altered regulation of metabolic pathways in human lung cancer discerned by 13C stable isotope-resolved metaolomics (SIRM)," Molecular Cancer, 8: 41, 19 pages (2009).
Faubert, B. et al., "Lactate metabolism in human lung tumors," Cell, 171(2): 358-371 (2017).
Fukumoto, S. et al., "Overexpression of the Aldo-Keto Reductase Family Protein AKR1B10 Is Highly Correlated with Smokers' Non-Small Cell Lung Carcinomas," Clinical Cancer Research, 11: 1776-1785 (2005).
Gaude, E. and C. Frezza, "Tissue-specific and convergent metabolic transformation of cancer correlates with metastatic potential and patient survival," Nature Communications, 7, Article No. 13041, 9 pages (2016).
Giménez-Dejoz, J. et al., "Substrate Specificity, Inhibitor Selectivity and Structure-Function Relationships of Aldo-Keto Reductase 1B15: A Novel Human Retinaldehyde Reductase," Edited by Fernando Rodrigues-Lima, PLOS One 10(7), 19 pages (Jul. 2015).
Grimshaw, C.E., "Aldose Reductase: Model for a New Paradigm of Enzymic Perfection in Detoxification Catalysts," Biochemistry, 31(42): 1 page (1992).
Hensley, C.T. et al., "Metabolic heterogeneity in human lung tumors," Cell, 164(4): 681-694 (Feb. 2016).
Jin, J. et al., "Aldo-keto Reductase Family 1 Member B10 Mediates Liver Cancer Cell Proliferation through Sphingosine-1-Phosphate," Scientific Report, 6: 22746, 11 pages (2016).
Li, S.S. et al., "Durable coexistence of donor and recipient strains after fecal microbiota transplantation," Science, 352(6285): 5 pages (2016).
MacLeod, A.K. et al., "Aldo-keto reductases are biomarkers of NRF2 activity and are co-ordinately overexpressed in non-small cell lung cancer," British Journal of Cancer, 115: 1530-1539 (2016).
Martin, Hans-Jörg and E. Maser, "Role of human aldo-keto-reductase AKR1B10 in the protection against toxic aldehydes," Chemico-Biological Interactions, 178: 145-150 (2009).
Mende, D.R. et al., "Accurate and universal delineation of prokaryotic species," Nature Methods, 8 pages (2013).
Mochalski, P. et al., "Release and uptake of volatile organic compounds by human hepatocellular carcinoma cells (HepG2) in vitro," Cancer Cell International, 13:72, 9 pages (2013).
Green et al., Molecular Cloning, A Laboratory Manual, Fourth Edition, vol. 1, Cold Spring Harbor Laboratory Press, 34 pages (2012).
Pavlova, N.N. and C.B. Thompson, "The Emerging Hallmarks of Cancer Metabolism," Cell Metabolism, 23(1): 27-47 (2016).
Petrash, J.M. et al., "Involvement of Cysteine Residues in Catalysis and Inhibition of Human Aldose Reductase," The Journal of Biological Chemistry, 267(34): 24833-24840 (1992).

(56) References Cited

OTHER PUBLICATIONS

Quince, C. et al., "Shotgun metagenomics, from sampling to sequencing and analysis," Nature Biotechnology, 35: 833-844 (2017).
Reznik, E. et al., "Mitochondrial DNA copy number variation across human cancers," eLIFE 5, 20 pages (2016).
Ross, B.M. et al., "The Use of SIFT-MS to Investigate Headspace Aldehydes as Markers of Lipid Peroxidation," Current Analytical Chemistry, 9: 600-613 (2013).
Schallschmidt, K. et al., "Investigation of cell culture volatilomes using solid phase micro extraction: Options and pitfalls exemplified with adenocarcinoma cell lines," Journal of Chromatography B, 1006: 158-166 (2015).
Sellers, K. et al., "Pyruvate carboxylase is critical for non-small-cell lung cancer proliferation," The Journal of Clinical Investigation, 125(2): 687-698 (2015).
Singh, A. et al., "Dysfunctional KEAP1-NRF2 Interaction in Non-Small-Cell Lung Cancer," PLOS Medicine, vol. 3, Issue 10, 1865-1876 (2006).
Sorek, R. et al., "Genome-wide experimental determination of barriers to horizontal gene transfer," Science, vol. 318, Issue 5855, pp. 1449-1452 (2007).
Srivastava, S. et al., "Aldose Reductase-catalyzed Reduction of Aldehyde Phospholipids," J Biol Chem, 279(15): 53395-53406 (2004).
Stockwell, B.R. et al., "Ferroptosis: a regulated cell death nexus linking metabolism, redox biology, and disease," Cell, 171(2): 273-285 (2017).
Tong, Y-H et al., "Keap1-Nrf2 pathway: A promising target towards lung cancer prevention and therapeutics," Chronic Diseases and Translational Medicine 1: 175-186 (2015).
Yan, R. et al., "Aldo-keto reductase family 1 B10 gene silencing results in growth inhibition of colorectal cancer cells: Implication for cancer intervention," Int. J. Cancer, 121: 2301-2306 (2007).
Yarza, P. et al., "Uniting the classification of cultured and uncultured bacteria and archaea using 16S rRNA gene sequences," Nature Reviews, 12: 635-645 (2014).
Yin, H. et al., "Free Radical Lipid Peroxidation: Mechanisms and Analysis," Chemical Reviews, 111: 5944-5972 (2011).
Yoshitake, H. et al., "Aldo-keto reductase family 1, member B10 in uterine carcinomas: a potential risk factor of recurrence after surgical therapy in cervical cancer," Int J Gynecol Cancer, 17: 1300-1306 (2007).
Zhao, D. et al., "Combinatorial CRISPR-Cas9 metabolic screens reveal critical redox control points dependent on the KEAP1-NRF2 regulatory axis," Mol Cell, 69(4): 699-708 (2018).
Zhou, Z. et al., "Inhibiting proliferation and migration of lung cancer using small interfering RNA targeting on Aldo-keto reductase family 1 member B10," Molecular Medicine Reports, 17: 2153-2160 (2018).
Applicant: Owlstone Med Ltd, Diagnosis of Cancer, Examination Report mailed Jul. 24, 2023 for EP Application No. 19766318 filed Sep. 4, 2019, 12 pages.
Zhou Y, et al., Expression of AKRs superfamily and prognostic in human gastric cancer, Feb. 22, 2023, 33041, 102(8), Jul. 13, 2023.
Amann et al., "Analysis of Exhaled Breath for Disease Detection", Annual Review of Analytical Chemistry, vol. 7, 2014, pp. 455-482.
Amann et al., "Analysis of Exhaled Breath for Screening of Lung Cancer Patients", Magazine of European Medical Oncology, vol. 3, No. 3, Oct. 1, 2010, pp. 106-112.
DeLano et al. "Volatile Decay Products in Breath During Peritonitis Shock are Attenuated by Enteral Blockade of Pancreatic Digestive Proteases", Shock, vol. 48, No. 5, 2017, pp. 571-575.
Gaude et al., "Targeted breath analysis: exogenous volatile organic compounds (EVOC) as metabolic pathway-specific probes," Journal of Breath Research, vol. 13, No. 3, May 17, 2019, 13 pages.
Modak et al., "A Rapid Non Invasive L-DOPA-13C Breath Test for Optimally Suppressing Extracerebral AADC Enzyme Activity—Toward Individualizing Carbidopa Therapy in Parkinson s Disease", J Parkinsons Dis., vol. 2, No. 4, Jan. 1, 2012, pp. 349-356.
Modak, "Breath biomarkers for personalized medicine", Personalized Medicine, vol. 7, No. 6, 2010, pp. 643-653.
O'Hara et al., "Limonene in exhaled breath is elevated in hepatic encephalopathy," Journal of Breath Research, 10 (2016) 046010, 11 pages.
Opdam et al., "The use of the 13C-dextromethorphan breath test for phenotyping CYP2D6 in breast cancer patients using tamoxifen: association with CYP2D6 genotype and serum endoxifen levels," Cancer Chemother. Pharmacol. (2013) 71: 593-601.
Opdam et al., "Further Characterization of a 13C-dextromethorphan breath test for CYP2D6 phenotyping in breast cancer patients on tamoxifen therapy," J. Breath Res. Apr. 2015. 20; 9(2):026003, Chapter 5, pp. 92-105.
Owlstone Medical, "Targeted breath analysis: exogenous volatile organic compounds (EVOC) as targeted metabolic proves in Breath Biopsy," Nov. 8, 2018, 49 pages.
Penning, "The aldo-keto reductases (AKRs): Overview," Chemico-Biological Interactions, vol. 234, Oct. 7, 2014, pp. 236-246.
Von Grafenstein et al., "Precursors for cytochrome P450 profiling breath tests from an in silico screening approach," J. Breath Res. 8 (2014) 046001, 14 pages.
GB Search Report for GB Application No. 1814346.1, titled "Diagnosis of Cancer," mailed on Mar. 25, 2019.
PCT International Search Report and Written Opinion for International Application No. PCT/GB2019/052468, titled "Diagnosis of Cancer," mailed on Dec. 3, 2019.
Database WPI, Week 200377, Jul. 30, 2003, Thomson Scientific, London, GB, XP002795937.
Database WPI, Week 201631, Mar. 16, 2016, Thomson Scientific, London, GB, XP002795938.
International Search Report and Written Opinion for International Application No. PCT/GB2019/051381, entitled Method to Evaluate Metabolic Activity of Liver Enzymes, consisting of 17 pages. Date Mailed: Sep. 19, 2020.
Fernandez Del Rio, R., et al, "Volatile Biomarkers in Breath Associated With Liver Cirrhosis—Comparisons of Pre- and Post-liver Transplant Breath Samples", Ebiomedicine, vol. 2, No. 9, pp. 1243-1250 (2015).
Chang, M., et al., "Interphenotype differences in disposition and effect on gastrin levels of omeprazole—suitability of omeprazole as a probe for CYP2C19," Br. J. Clin. Pharmacol. 39, 511-518 (1995).
De Kesel, P.M.M., et al., "Alternative Sampling Strategies for Cytochrome CYP450," Phenotyping. Clin. Pharmacokinet. 55, 169-184 (2016).
Lin, Y.S., et al., "In-vivo phenotyping for CYP3A by a single-point determination of midazolam plasma concentration. Pharmacogenetics," 11, 781-791 (2001).
Ned Mmsc Phd, R.M., "Genetic testing for CYCYP450 polymorphisms to predict response to clopidogrel: current evidence and test availability," Application: pharmacogenomics. PLoS Curr. 2 (2010).
Ou-Yang, D.S., et al., "Phenotypic polymorphism and gender-related differences of CYP1A2 activity in a Chinese population," Br. J. Clin. Pharmacol. 49, 145-151 (2000).
Pijls, K.E., et al., "Critical appraisal of 13 C breath tests for microsomal liver function: aminopyrine revisited," Liver Int. 34, 487-494 (2014).
Sachse, C., et al., "Cytochrome CYP450 2D6 variants in a Caucasian population: allele frequencies and phenotypic consequences," Am. J. Hum. Genet. 60, 284-295 (1997).
Samer, C.F., et al., "Applications of CYCYP450 testing in the clinical setting," Mol. Diagn. Ther. 17, 165-184 (2013).
Tanaka, E., et al., "How useful is the "cocktail approach" for evaluating human hepatic drug metabolizing capacity using cytochrome CYP450 phenotyping probes in vivo?" J. Clin. Pharm. Ther. 28, 157-165 (2003).
Thacker, D.L., et al., "Is (+)-[13 C]-pantoprazole better than (±)-[ 13 C]-pantoprazole for the breath test to evaluate CYP2C19 enzyme activity?," J. Breath Res. 7, 16001 (2012).
Thakur, M., et al., "Review of evidence for genetic testing for CYCYP450 polymorphisms in management of patients with nonpsychotic depression with selective serotonin reuptake inhibitors," Genet. Med. 9, 826-835 (2007).

(56) References Cited

OTHER PUBLICATIONS

Zanger, U.M., et al., "Cytochrome P450 enzymes in drug metabolism: Regulation of gene expression, enzyme activities, and impact of genetic variation," Pharmacol. Ther. 138, 103-141 (2013).
Great Britain Search Report, Application No. GB1808062.2, Date of Search: Dec. 12, 2018, 5 pages.
GB Search Report for GB Application No. 1814350.3, titled "Diagnosis of Cancer," mailed on Feb. 20, 2019.
Restriction Requirement from U.S. Appl. No. 17/055,914, consisting of 5 pages. Dated Apr. 26, 2023.
Final Rejection Mailed on May 30, 2024, entitled "Method to Evaluate Metabolic Activity of Liver Enzymes" for U.S. Appl. No. 17/055,914, 15 page(s).
Masyita et al. Food Chemistry, entitled "Terpenes and terpenoids as main bioactive compounds of essential oils, their roles in human health and potential application as natural food preservatives," X13, 100217, 1-14 (Year: 2022).
Bacanli et al. The antioxidant and antigenotoxic properties of citrus phenolics limonene and naringin, Food and Chemical Toxicology, 2015, 81, 160-170 (Year: 2015).
Barski et al Drug Metab. Rev., 2008, 40, 553-624 (Year: 2008).
EP Response to Office Action dated Nov. 27, 2023, EP Application 19766318.0, entitled Diagnosis of Cancer, Applicant Owlstone Medical Limited, 4 pages.
Fernandez del Rio et al. EBioMedicine, 2015, 2, 1243-1250 (Year: 2015).
Goh et al. PLOS One, 2017, 12, 1-16 (Year: 2017).
Hung et al., Prognostic significance of AKR1B10 in patients with resected lung adenocarcinoma, Accepted Aug. 13, 2018, Thoracic Cancer, 1492-1499, 9, Retrieved Jun. 27, 2018.
Lu et al., Diagnostic value of aldo-keto reductase family 1 member B10 in human nasopharyngeal carcinoma, Accepted Aug. 21, 2023, Molecular and Clinical Oncology, 7 pages, 19:89.
Non-Final Office Action received for U.S. Appl. No. 17/055,914, mailed on Nov. 6, 2023, 16 pages.
Abruzzese F. et al., "Lack of correlation between mRNA expression and enzymatic activity of the aspartate aminotransferase isoenzymes in various tissues of the rat", FEBS Letters, vol. 366, No. 2-3, Jun. 12, 1995, pp. 170-172.
Chang T. K. et al., "Real-Time Polymerase Chain Reaction Analysis CYP1 B1 Gene Expression in Human Liver", Review of Economic Dynamics, vol. 71, No. 1, Jan. 1, 2003, pp. 11-19.
Ferreira Leal, Mariana et al., "Targeting tumour-associated aldo-keto reductase activity with exogenous volatile organic compound (EVOC) Probes to detect lung cancer", Jun. 20, 2022, pp. 1-1.

\* cited by examiner

DIAGNOSIS OF CANCER

This application is the U.S. National Stage of International Application No. PCT/GB2019/052468, filed on Sep. 4, 2019, which designates the U.S., published in English, and claims priority under 35 U.S.C. § 119 or 365 (c) to GB Application No. 1814350.3, filed on Sep. 4, 2018. The entire teachings of the above applications are incorporated herein by reference.

INTRODUCTION

Early diagnosis of cancer remains an important goal in any treatment plan. Cancer that is diagnosed at an early stage is more likely to be treated successfully. If the cancer spreads, effective treatment becomes more difficult, and generally a person's chances of surviving are much lower.

Lung cancer is the second most prevalent cancer in adult men and women around the world. The prognosis and treatment options of lung cancer patients depend directly on tumor size and its spread at the time of diagnosis; survival time decreases significantly as the disease is more progressive at detection. Therefore, early detection of lung cancer is paramount and there is a need for non-invasive and reliable screening techniques. More than 80% of lung cancer patients will survive for at least a year if diagnosed at the earliest stage compared to around 15% for people diagnosed with the most advanced stage of disease.

Other examples of the benefits of early detection apply to breast cancer, ovarian cancer and bowel cancer. More than 90% of women diagnosed with breast cancer at the earliest stage survive their disease for at least 5 years compared to around 15% for women diagnosed with the most advanced stage of disease.

Whilst early detection of cancer is paramount, there are few non-invasive test methods available which enable a reliable diagnosis whilst increasing patience compliance due to the convenient testing methods. Moreover, there is also a need for monitoring the progression of cancer in a reliable and non-invasive way to determine treatment options.

Exhaled breath contains low concentrations of various volatile organic compounds (VOCs) produced by the body. These are believed to reflect endogenous metabolic processes at the tissue level, such as inflammation and oxidative stress. When cancer develops, metabolic changes can create a unique endogenous VOC profile that is potentially reflected in the body fluids, including breath. Detection of cancer by analysing exhaled breath has therefore become an area of interest as it allows the development of non-invasive detection techniques. However, whilst a large number of exhaled VOCs have been identified, it is difficult to identify VOCs that are excreted in breath and that are indeed specific to a particular cancer to provide a reliable diagnosis.

Endogenous VOC compounds are by-products of specific metabolic pathways that are likely to be affected by several physiological and pathological factors. Endogenous VOCs can be a reliable readout for the activity of internal metabolic processes—acetone and isoprene are good markers for ketosis and blood cholesterol, respectively. However, as these metabolic processes are altered by several pathological conditions and physiological factors, the association of endogenous breath VOCs to specific diseases is complicated. Moreover, breath secretion of endogenous VOCs is the cumulative result of metabolic reactions occurring in different tissues. While specific diseases may alter the function of individual tissues and organs, this effect can be challenging to detect when monitoring the sum contribution of healthy and diseased tissues in breath. This aspect significantly complicates the task of identifying the tissue of origin of specific breath VOCs.

The interpretation of endogenous breath VOCs as disease biomarkers is also complicated by the effect of exogenous VOCs deriving from recent or past exposures. Breath VOCs that can derive from endogenous metabolic processes, such as ethane, can also derive from environmental exposure, as well as from metabolism of gut microbiota. Ultimately, this remains a potential pitfall of breath analysis and disentangling the effect of previously encountered exogenous VOCs during the discovery of breath biomarkers for disease is a complicated task.

Thus, there has so far not been a clinical adoption of breath analysis methods for diagnosis of cancer because of the lack of cancer specific VOC markers for reliably predicting a cancer disease state.

Cancer cells are known to undergo profound metabolic changes to support survival, proliferation, immune escape and metastasis (Pavlova and Thompson 2016; Gaude and Frezza 2016). For instance, lung cancer cells have been shown to increase glucose and lactate consumption in order to feed carbon flow into mitochondria (Fan et al. 2009; Sellers et al. 2015; Faubert et al. 2017; Hensley et al. 2016). The activation of mitochondrial metabolism is a peculiar mechanism activated almost exclusively by lung cancer cells (Reznik et al. 2016) and it has been shown to support the synthesis of glutathione (GSH) (Fan et al. 2009), a fundamental regulator of oxidative stress.

Redox regulation and activation of antioxidant mechanisms are at the core of lung cancer formation and survival, as evidenced by the fact that 20-40% of human lung cancers select for mutations of Kelch-like ECH-associated protein 1 (KEAP1), a negative regulator of Nuclear factor erythroid-2 related factor 2 (NRF2) (Singh et al. 2006). This results in stabilisation of NRF2 and activation of a strong antioxidant response that includes increased activity of antioxidant enzymes and increased levels of glutathione (Singh et al. 2006). In line with this evidence, oncogenic mutations affecting KRAS, B-RAF, and c-Myc lead to upregulation of NRF2 and drive tumourigenesis in vivo via a mechanism that involves reactive oxygen species (ROS) regulation (DeNicola et al. 2011), demonstrating that multiple cancer mutations converge towards redox control as a common mechanism of cancer formation.

This indicates that metabolic changes distinguish lung cancer from normal cells, as well as from other cancer cells in vivo. Many of these metabolic changes are known to converge in the oxidative stress and redox control pathways.

High levels of oxidative stress damage cancer cells increasing the risk of cell death. Among the survival strategies adopted by lung cancer cells to prevent this is the activation of protective mechanisms against ferroptosis, a form of regulated cell death induced by the accumulation of lipid peroxidation products via ROS- and iron-dependent reactions (Stockwell et al. 2017; Alvarez et al. 2017). Nitrogen fixation S. cerevisiae homolog 1 (NFS1) is induced in well-differentiated, early-stage lung tumours, to provide Fe—S clusters to cancer cells and suppress iron-induced lipid peroxidation and ferroptosis. Suppression of NFS1 alone, or in combination with inhibition of antioxidant mechanisms, can significantly impair lung tumour formation in vivo (Alvarez et al. 2017). Control of lipid peroxidation is therefore fundamental for lung cancer cells to avoid ferroptosis and survive.

Among the enzymes that are activated by lung cancer cells to control lipid peroxidation, aldo-keto reductases (AKRs) are of great importance due to their inducible regulation. Pharmacological induction of lipid peroxidation and ferroptosis in vitro is followed by several 100-folds induction in the expression of members of the AKR enzyme superfamily, indicating that AKRs can function as a response mechanism to lipid peroxidation (Dixon et al. 2014). Members of the AKR1B family are direct targets of the transcriptional activation orchestrated by NRF2 (Nishinaka et al. 2017), the master antioxidant transcription factor on which several oncogenic mutations converge to ensure survival of lung cancer cells (DeNicola et al. 2011). In addition, some AKR isoforms bear a hyperreactive cysteine residue at the enzyme active site (Cys-298) which can be oxidised by ROS, accelerating the catalytic activity of the enzyme, as well as blocking inhibitor binding (Petrash et al. 1992). This evidence indicates that AKRs are an integral part of the antioxidant response activated against lipid peroxidation, a fundamental mechanism for survival of lung cancer cells.

AKRs catalyse oxidation-reduction reactions on a wide variety of substrates including glucocorticoids, carbonyl metabolites, glutathione conjugates, and phospholipid aldehydes, among others (Barski, Tipparaju, and Bhatnagar 2008). Given the wide diversity of biological substrates, it appears that AKRs may have the common function of detoxification of aldehydes and ketones produced by endogenous metabolic reactions, as well as environmental toxins encountered via food, medications or other sources (Bachur 1976). Using pyridine nucleotides as cofactors, most AKRs catalyse reduction of aldehydes and ketones, while being relatively inefficient alcohol dehydrogenases (Barski, Tipparaju, and Bhatnagar 2008). NADPH is the preferred cofactor, compared to NADH, indicating that maintenance of high levels of cytoplasmic NADPH is required for AKR activity. This is an important aspect in lung cancer biology, as NADPH synthesis depends on availability of GSH, and indicates a link between increased GSH production and high AKR activation in lung cancer cells.

Most of the energy required for carbonyl reduction by AKRs is obtained from nucleotide cofactor binding, rather than substrate binding, resulting in highly efficient reduction of substrates, even when loosely bound to the active site. This explains the wide range of substrates that some AKR families, such as AKR1B family, can act on (Grimshaw 1992), and justifies the pivotal role of AKRs as detoxifying enzymes. The carbonyl group present in aldehydes is very reactive and can readily attack nucleophilic centres, such as protein aminoacids and membrane phospholipids. The reduction of aldehydic carbonyls into alcohols by AKRs reduces the overall chemical reactivity of the molecule, and is one of the mechanisms of detoxification of reactive aldehydes from the cell (Barski, Tipparaju, and Bhatnagar 2008). Lipid peroxidation can give rise to a wide range of different toxic aldehydes, because ROS can oxidise any bisallylic group in the lipid chain (Ayala, Muñoz, and Argüelles 2014; Yin, Xu, and Porter 2011). Furthermore, it is considered that aldehydes are the major by-product of lipid peroxidation (Barski, Tipparaju, and Bhatnagar 2008). The wide range of substrate-specificity, together with the ability to readily reduce reactive aldehydes, makes the AKRs family an ideal antioxidant mechanism against lipid peroxidation and ferroptosis. In support of this hypothesis, AKRs have been shown to reduce products of lipid peroxidation, such as 4-hydroxynonenal (Giménez-Dejoz et al. 2015; Martin and Maser 2009), as well as PAPC and POVPC (Srivastava et al. 2004).

In line with the need of cancer cells to control lipid peroxidation and ferroptosis, members of the AKRs superfamily have been found increased in different cancer types. For instance, AKR1B10 is increased in lung, liver, colorectal, and uterine cancers (Yoshitake et al. 2007; Cao, Fan, and Chung 1998; Fukumoto 2005). Genetic suppression of AKR1B10 in colorectal cancer cells reduce survival, foci formation and colony size, indicating that this enzyme is required for cancer cell survival (Yan et al. 2007). Increase of lipid peroxidation, and concomitant mechanisms for its control, are considered an early event during lung cancer formation (Zhao et al. 2018; Alvarez et al. 2017; Tong et al. 2015), suggesting that detection of these molecular events could help in the early diagnosis of lung cancer (and potentially offering a tool to distinguish between benign and malignant lesions). In addition, the expression of AKR1B10 is increased several folds in lung cancer compared to normal lung epithelium (MacLeod et al. 2016). AKR1B10 is functionally different from the ubiquitously expressed AKR1C family present in normal lung tissue.

Members of the AKR1B family have been shown to act on several, highly volatile, compounds. Indeed AKR1B1, AKR1B10 and AKR1B15 have shown substrate-specificity for the volatile aldehydes benzaldehyde and cinnamaldehyde, the alkanal hexanal, the alkenals 4-hydroxynonenal, hexenal, and farnesal, the ketones 3-nonen-2-one, and the dicarbonyls 2,3-butanedione and 2,3-hexanedione, among others (Giménez-Dejoz et al. 2015). This evidence suggests that increased expression of AKRs in cancer could result in increased reduction of specific VOCs and production of corresponding ketones or alcohol derivatives. For instance, the lung cancer cell line A549 and the hepatocellular carcinoma cell line HepG2 display increased expression and activity of the enzyme AKR1B10 (Zhou et al. 2018; Jin et al. 2016). Headspace analysis of A549 cells showed decreased levels of propanal, an aldehyde that can be produced during lipid peroxidation (Ross et al. 2013), together with increased levels of the alcohol propanol (Schallschmidt et al. 2015). A similar study performed on HepG2 cells showed decreased levels of hexanal, another aldehyde produced by lipid peroxidation (Ross et al. 2013), and increased levels of several ketones (Mochalski et al. 2013).

The present invention is aimed at addressing the need for reliable non-invasive screening methods for early detection of cancer.

SUMMARY

In a first aspect, the invention relates to a method for the detection of cancer, such as lung cancer, comprising assessing the activity of a cancer-specific enzyme, such as an AKR enzyme, by measuring the concentration of an exogenous substrate for said enzyme and/or measuring the concentration of a metabolite of said substrate in exhaled breath of a subject.

The invention also relates to a method for monitoring the progression of cancer, such as lung cancer, in a subject diagnosed with said cancer comprising assessing the activity of a cancer-specific enzyme, such as an AKR enzyme, by measuring the concentration of an exogenous substrate for said enzyme and/or measuring the concentration of a metabolite of said substrate in exhaled breath of the subject.

Another aspect relates to a method for determining efficacy of a treatment in a subject diagnosed with cancer, such as lung cancer, comprising assessing the activity of a cancer-specific enzyme, such as an AKR enzyme, by measuring the concentration of an exogenous substrate for said enzyme and/or measuring the concentration of a metabolite of said substrate in exhaled breath of the subject wherein said subject has received anti-cancer treatment.

Another aspect relates to a system for the detection of cancer, such as lung cancer, comprising assessing the activity of a cancer-specific enzyme, such as an AKR enzyme, by measuring the concentration of an exogenous substrate for said enzyme and/or measuring the concentration of a metabolite of said substrate in exhaled breath of a subject wherein said system comprises a device for capturing a breath sample from a patient.

Another aspect relates to a kit comprising the system above.

In one embodiment of the methods, system and kit, the substrate and/or its metabolite is a VOC, for example a GRAS compound. In one embodiment, the substrate is labelled or not labelled. The cancer may be selected from lung cancer, breast cancer, ovarian cancer, bowel cancer, prostate cancer, bladder cancer, colorectal cancer, pancreas carcinoma, kidney cancer, renal cancer, leukaemias, multiple myeloma, lymphomas (e.g. Hodgkin's disease and non-Hodgkin's Lymphoma), brain cancer and other CNS and intracranial tumours cancer, head and neck cancer, oesophageal cancers, solid tumors such as sarcoma and carcinomas, mesothelioma, osteosarcoma, endometrial cancer or melanoma.

In one embodiment, the cancer is lung cancer and the enzyme is a lung cancer-specific enzyme. In one embodiment, lung cancer is selected from small cell lung cancer, non-small cell lung cancer, squamous cell carcinoma or adenocarcionoma. In one embodiment, the lung cancer-specific enzyme is an aldo-keto reductase (AKR). In one embodiment, the aldo-keto reductase is AKR1B10 or AKR1B15. In one embodiment, the substrate is labelled retinaldehyde. In one embodiment, the label is 12C, 13C, 14C, 2H, 14N or 18O. In one embodiment, the substrate is cinnamaldehyde. In one embodiment, the method comprises establishing a subject value based on a concentration of said substrate or metabolite. In one embodiment, the subject value is compared to one or more reference value and wherein a difference in the subject value and a reference value indicates a likelihood of cancer. In one embodiment, the reference value is the value of a subject that has been diagnosed with cancer. In one embodiment, the reference value is the value of a healthy subject. In one embodiment, the concentration of two or more exogenous substrates and/or the concentration of two or more metabolites is measured.

FIGURES

The invention is further described in the following non-limiting figures.

FIG. 1. mRNA analysis of lung adenocarcinoma (LUAD) and lung squamous carcinoma (LUSC), compared to corresponding normal lung tissues. Volcano plots show the fold variation (x axis) and statistical significance (y axis, −log 10(p-value)) of the comparisons LUAD vs Normal (left) and LUSC vs normal (right). Red dots indicate different AKR isoforms. AKR1B10 and AKR1B15 are highlighted.

Figure 2:
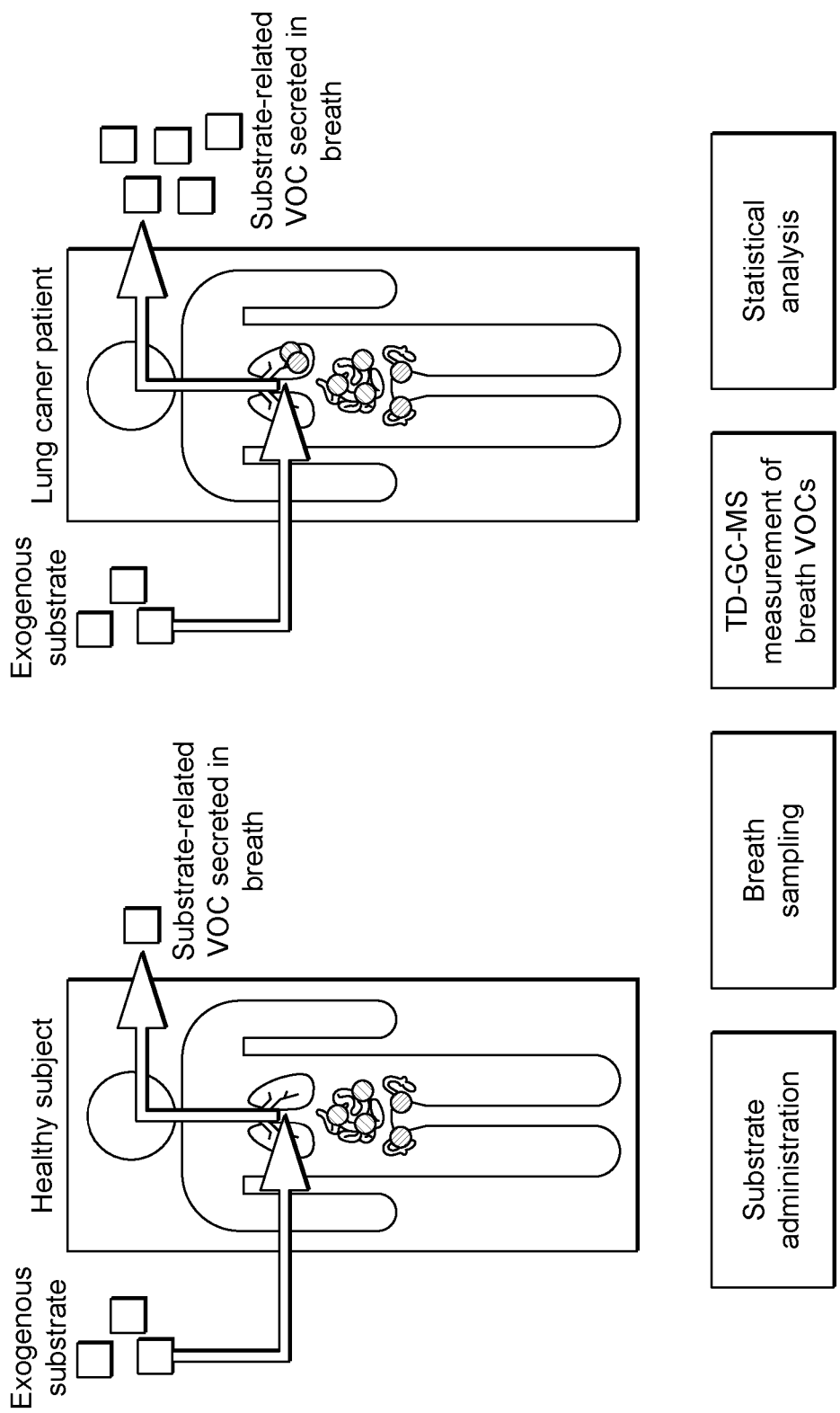

FIG. 2. Workflow of measuring substrate-related VOC(s) in breath.

Figure 3A:
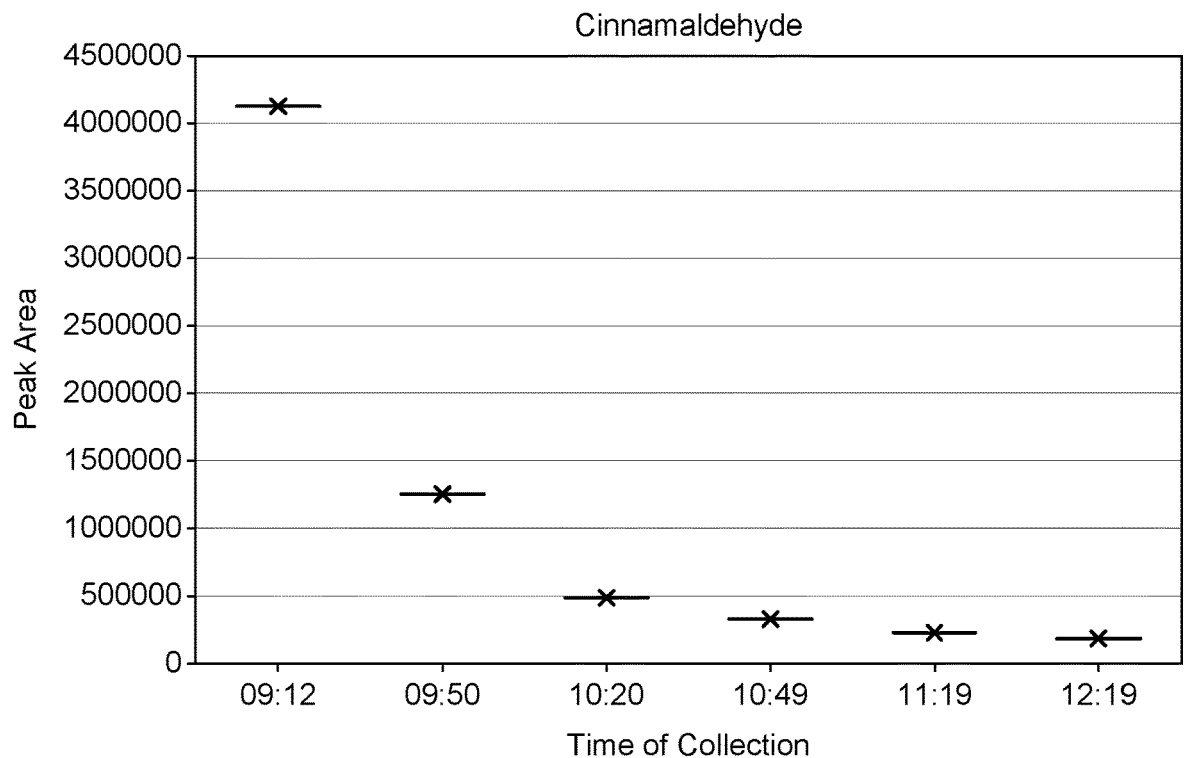
Figure 3B:
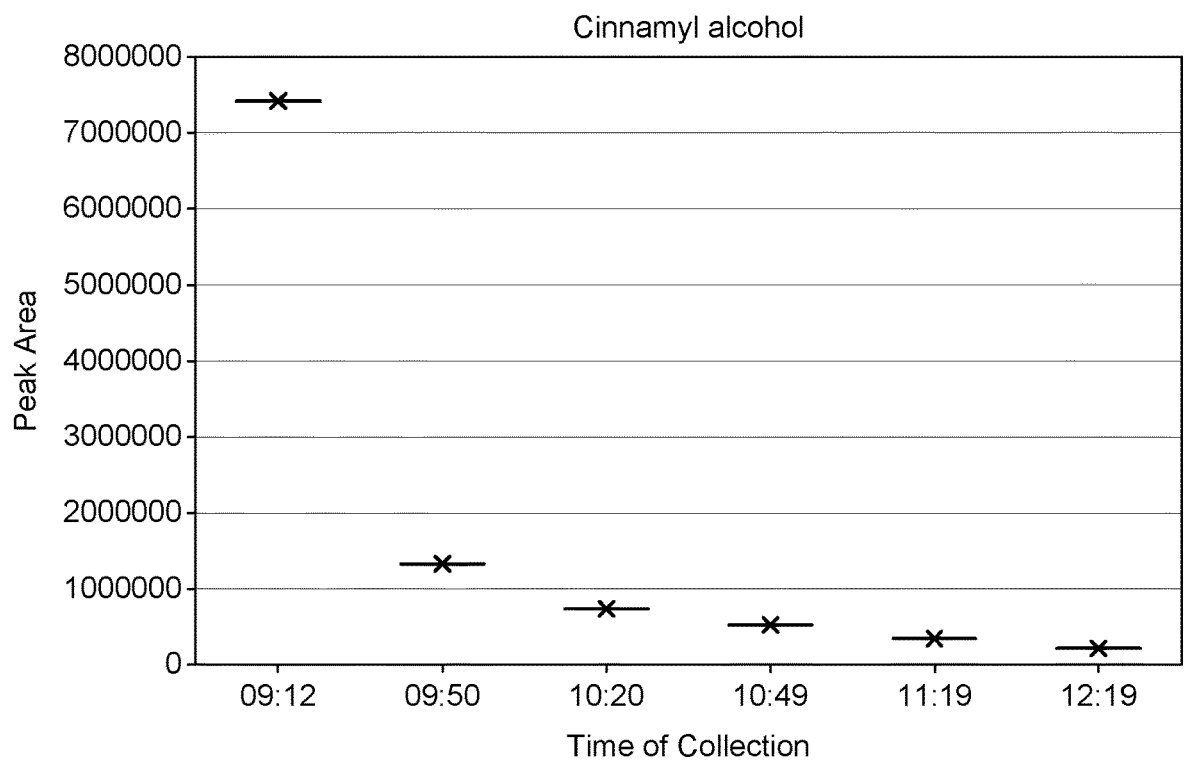

FIG. 3. Measurement of cinnamaldehyde (3a) and cinnamyl alcohol (3b).

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The invention provides a non-invasive method of detecting, diagnosing or screening for cancer in a subject or making a prognosis as to the likelihood that the subject will develop cancer. In particular, the invention provides a method for the early detection and monitoring of the progression of cancer by detecting breath biomarkers.

Endogenous VOCs as biomarkers for the detection of cancer in breath have been reported. However, as mentioned above, the detection of certain VOCs in breath does not provide a reliable diagnosis. In contrast to methods that rely on the detection of endogenous substances, the invention is based on using an exogenous substrate that can be directly used as a cancer probe by monitoring the breath clearance (or washout) of a VOC substrate itself, and/or by detecting a VOC metabolic product derived from metabolism of the substrate. This method makes use of an exogenous substance, e.g. a VOC that, metabolised by the subject, provides a readout of metabolic enzymes/organs.

Cancer cells exhibit uniform metabolic abnormalities, termed the cancer metabolic phenotype. The mechanisms can be associated with (1) oncogenesis; (2) rapid reproduction; (3) stress responses; (4) invasiveness and metastasis; (5) resistance to host immune surveillance; (6) resistance to therapy. It is known that certain enzymes are cancer-specific. The invention is therefore based on monitoring the metabolic activity of a cancer-specific enzyme, in particular an AKR enzyme, by providing an exogenous substrate (also termed reactant herein) which is metabolised by the cancer-specific enzyme. The presence of the substrate and/or its breakdown product (metabolite) in exhaled breath is detected, thereby detecting the presence of cancer. Provision of an exogenous substrate that is metabolised by a cancer-specific mechanism thus results in differential secretion in exhaled breath of the substrate itself and/or of its metabolites in breath of diseased subjects compared to healthy subjects.

Assessing metabolic activity of cancer-specific enzymes through a breath test as described herein can be used to make inferences about the presence, absence or progression of cancer (cancer disease state) in a test subject. Such a test can therefore be used for the diagnosis of cancer, predicting progression of cancer and/or determining treatment of cancer.

Thus, in a first aspect, the invention relates to a method for the detection or prognosis of cancer or monitoring the status of cancer comprising assessing the activity of a cancer-specific enzyme, in particular an AKR enzyme, by measuring the concentration of an exogenous substrate for said enzyme, and/or measuring the concentration of a metabolite of said substrate deriving from the enzymatic conversion of the cancer-specific enzyme, in exhaled breath of a subject.

Without wishing to be bound by theory, the inventors have found that AKRs can serve as a powerful tool for early detection of cancer via breath analysis for several reasons: i) cancer cells, such as lung cancer cells, adopt unique metabolic changes to support, among others, activities of AKRs, suggesting that cancer cells may be identified based on such metabolic adaptations; ii) induction of lipid peroxidation and mechanisms to control ferroptosis, among which AKRs play a pivotal role, are early event in lung cancer, among other cancers, suggesting that detection of AKRs could reveal early tumourigenic lesions; iii) AKR isoforms are ectopically overexpressed in different forms of cancer, allowing for assessment of cancer-specific enzymatic activity, potentially reducing the effect of surrounding normal tissue; iv) AKRs can generate volatile organic compounds, thus allowing for analysis of their activity in human breath.

Thus, the method is based on using an exogenous substrate that is biotransformed by a cancer-specific enzyme. A cancer-specific enzyme as used herein is an enzyme that is selected from one or more of the following: the enzyme is absent in cancer tissue, but present in non-cancer tissue; the enzyme is present in cancer tissue, but absent in non-cancer tissue; the enzyme is differentially expressed or in cancer tissue compared to non-cancer tissue or the enzyme is differentially active in cancer tissue compared to non-cancer tissue. For example, the enzyme may be expressed at a higher level in cancer tissue or lower level compared to expression in non-cancer tissue. Expression can be measured by techniques known in the art, for example by mRNA quantification or measuring cDNA. Non-cancer tissue refers for example to healthy tissue. The tissue may be from a specific organ, e.g. lung, colon, breast, prostate etc.

Thus, methods described herein measure the activity of enzymes that are directly associated with a cancer disease state in a non-invasive way by measuring their metabolic activity and analysing breath biomarkers. Due to the association between the enzyme and the cancer disease state, a diagnosis or prognosis can be made as to the patient's disease state. On that basis, a suitable treatment can be selected.

Metabolism and transformation of the substrate by one or more cancer-specific enzyme leads to the generation of a breakdown product, that is a metabolic product, i.e. a metabolite. Soon after provision of the substrate to the subject, the substrate is excreted into breath at high levels and clearance of the substrate from breath occurs as a consequence of biotransformation of the substrate by the action of one or more cancer-specific enzymes (washout of the reactant). For example, the kinetic profile of the clearance of the substrate from breath is used as a readout of the cancer-specific enzyme activity responsible for biotransformation of said substrate.

In addition, metabolism of a specific substrate through one or more cancer-specific enzyme leads to production of enzyme-specific metabolic products. As opposed to washout curves of the substrate, metabolic products are excreted into breath over time, starting at low levels and increasing over time due to biotransformation of the substrate by the cancer-specific enzyme. Measurement of such a metabolic product can be applied as a probe for assessing the metabolic phenotype of the enzyme or enzymes responsible for the production of said product. Measuring a substrate and corresponding metabolic product(s) in exhaled breath can thus be used either alone or in combination to assess the activity of one or more cancer-specific enzyme.

Therefore, the method enables the testing of multiple compounds in exhaled breath. This allows testing for the presence of more than one type of cancer. Furthermore, multiple compounds can be measured in exhaled breath which are specific to a certain type of cancer, thereby enabling a more accurate diagnosis due to multiple parameters that are assessed. In one embodiment, the invention therefore relates to a method for the detection of cancer comprising assessing the activity of one or more cancer-specific enzyme by measuring the concentration of two or more exogenous substrates for said enzyme and/or measuring the concentration of two or more metabolites of said substrate(s) in exhaled breath of a subject. In one embodiment, the invention also relates to a method for the detection of cancer comprising assessing the activity of more than one cancer-specific enzyme expressed in different tissue by measuring the concentration of two or more exogenous substrates for said enzymes and/or measuring the concentration of two or more metabolites of said substrate(s) in exhaled breath of a subject. The method of the invention can therefore be a multiplex method enabling assessment of multiple enzymatic activities simultaneously in the same breath sample(s).

In one embodiment of the various methods of the invention, the enzyme is an AKR enzyme, for example selected from AKR1B10 or AKR1B15. As explained above, cancer cells undergo metabolic changes that converge in the oxidative stress and redox control pathways. AKRs are an integral part of the antioxidant response activated against lipid peroxidation, a fundamental mechanism for survival of lung cancer cells. Assessing their activity is therefore of diagnostic importance. Expression of members of the AKR superfamily is increased in different cancer types. For example, expression of AKR1B10 is significantly increased in lung cancer cells compared to normal cells. This allows differential detection of lung cancer A "subject" as used herein refers to a test subject, e.g. a mammalian subject, preferably a human. In one embodiment, a sample of exhaled breath is obtained from the subject for the purpose of diagnosing or screening the presence/absence of a cancer disease state or making a prognosis as to the likelihood that the subject will develop cancer. The subject may be male or female. The subject may be an infant, a toddler, a child, a young adult, an adult or a geriatric. The subject may be a smoker, a former smoker or a non-smoker. The subject may have a personal or family history of cancer. The subject may have a cancer-free personal or family history. The subject may exhibit one or more symptoms of cancer.

If the cancer screened for is lung cancer, the subject may exhibit one or more symptoms of other lung disorder (e.g., emphysema, COPD). For example, the subject may have a new or persistent cough, worsening of an existing chronic cough, blood in the sputum, persistent bronchitis or repeated respiratory infections, chest pain, unexplained weight loss and/or fatigue, or breathing difficulties such as shortness of breath or wheezing. The subject may have a lesion, which may be observable by computer-aided tomography or chest X-ray. The subject may be an individual who has undergone a bronchoscopy or who has been identified as a candidate for bronchoscopy (e.g., because of the presence of a detectable lesion or suspicious imaging result).

As used herein, a "healthy subject" is defined as a subject that does not have a diagnosable cancer disease state, for example does not have a lung cancer.

A "test subject value" is the value obtained in a test subject, i.e. a subject that is being assessed for cancer. The test value is the concentration of the metabolite and/or substrate that is measured in exhaled breath.

As used herein, "reference value", "baseline" or "threshold value" means a value determined by performing the testing method on one or more, preferably a plurality of reference subjects. A reference subject can be a healthy subject or a subject diagnosed with a cancer, e.g. a lung cancer.

"Risk assessment" refers to the relative risk an individual faces with respect to mortality. For example, a prognosis providing a high risk assessment for e.g. a 5-year mortality has a greater likelihood of mortality within 5 years than an individual having a low risk assessment for 5-year mortality.

In one embodiment, the prognosis for long term mortality is "high risk," e.g., high risk of mortality, "intermediate risk," e.g., intermediate risk of mortality, or "low risk," e.g., low risk of mortality. The stage of cancer and the prognosis may be used to tailor a patients therapy to provide a better outcome, e.g., systemic therapy and surgery, surgery alone, or systemic therapy alone. Risk assessment can be divided as desired, e.g., at the median, in tertiary groups, quaternary groups, and so on.

A "likelihood of a cancer disease state" means that the probability that the cancer disease state exists in the subject specimen is about 50% or more, for example 60%, 70%, 80% or 90%.

"Prognosis" refers, e.g., to overall survival, long term mortality, and disease free survival. In one embodiment, long term mortality refers to death within 5 years after diagnosis of lung cancer.

"Therapeutic treatment" and "cancer therapies" refers to chemotherapy, hormonal therapy, radiotherapy, immunotherapy, and biologic (targeted) therapy.

As used herein, a "substrate" or "reactant" refers to a chemical compound that is recognized by the cancer-specific enzyme of interest, e.g. and AKR enzyme, and for which the enzyme catalyzes conversion of the substrate into a different chemical compound which is referred to herein as a "metabolite". The substrate used in the methods of the invention is an exogenous substance, i.e. a xenobiotic. The terms exogenous substance or xenobiotic refer to a substance that is foreign to the subject's body; i.e. not produced by the subject, and which is preferably specifically and selectively metabolised by the cancer-specific enzyme. Preferably, the exogenous substance is converted into a metabolite by the cancer-specific enzyme that is also a xenobiotic, that is it does not normally occur in the subject's body.

The method may comprise the step of providing the exogenous substrate to the subject. Thus, in one embodiment, the method includes the step of administering the substrate to a subject. Administration may by any convenient route, including but not limited to oral, topical, parenteral, sublingual, rectal, vaginal, ocular, intranasal, pulmonary, intradermal, intravitrial, intramuscular, intraperitoneal, intravenous, subcutaneous, intracerebral, transdermal, transmucosal, or topical, particularly to the ears, nose, eyes, or skin or by inhalation. Parenteral administration includes, for example, intravenous, intramuscular, intraarterial, intraperitoneal, intranasal, rectal, intravesical, intradermal, topical or subcutaneous administration. Preferably, the compositions are administered orally, for example as a liquid, capsule or tablet, such as a slow release formulation. A skilled person would know that the route of administration depends on the enzyme and cancer tested. For instance, if the target enzyme is present in the gastrointestinal tract, oral administration is preferable, while in case of hepatic expression either oral or intravenous administration could constitute viable options. In the case of lung cancer, the enzyme can be administered via oral administration or inhalation.

In one embodiment, said substrate and/or its metabolite is a VOC that is secreted in exhaled breath, preferably a VOC that is secreted in exhaled breath at high proportions and preferably a VOC that can be measured in breath without the use of any labels, such as isotope labels.

The term VOC refers to any compound of carbon, excluding carbon monoxide, carbon dioxide, carbonic acid, metallic carbides or carbonates and ammonium carbonate, which participates in atmospheric photochemical reactions but excluding carbon monoxide, carbon dioxide, carbonic acid, metallic carbides or carbonates, and ammonium carbonate. Generally, VOCs are defined as organic chemical compounds whose composition makes it possible for them to evaporate under normal indoor atmospheric conditions of temperature and pressure. Since the volatility of a compound is generally higher the lower its boiling point temperature, the volatility of organic compounds is sometimes defined and classified by their boiling points. Volatile compounds are compounds that are secreted by the human body into gas fluids, including for example breath, skin emanations and others. In one embodiment, a VOC is any organic compound having an initial boiling point less than or equal to about 250° C. measured at a standard atmospheric pressure of about 101.3 kPa.

According to the various aspects of the invention, in one embodiment, the substrate may be a VOC and the concentration of the exhaled VOC substrate in breath is measured.

Thus, the method uses an exogenous volatile organic compound (EVOC) as tracers of specific in vivo cancer-specific metabolic activities. EVOCs can be volatile compounds that, administered to a subject through various routes, undergo metabolism and distribution in the body and are excreted via breath. Additionally, metabolism of EVOCs by cancer-specific enzymes can lead to production of other volatile compounds that can also be detected in breath.

In one embodiment, the substrate is a VOC and its metabolite is not a VOC. In another embodiment, the substrate is not a VOC and its metabolite is a VOC. In this case, the concentration of the metabolite in breath is measured. In another embodiment, the substrate is a VOC and its metabolite is a VOC. In this case, the concentration of the substrate and/or the metabolite in breath is measured.

If the substrate is a VOC, it may be labelled or it may not be labelled.

The VOC that is measured according to the methods is not naturally occurring/produced by the subject and exhaled in breath. This ensures that any readings are not contaminated by endogenous VOCs that are naturally produced and can be found in exhaled breath.

In one embodiment, the substrate is a naturally occurring compound (but that is not endogenously produced), for example a food compound. This has the advantage that it can be provided to a subject without the occurrence of side effects. In one embodiment, the substrate does not have any therapeutic benefit. In one embodiment, the substrate is not a non-naturally occurring compound.

In one embodiment, the substrate is a GRAS compound, for example a GRAS compound that is a VOC. "GRAS" is an acronym for the phrase Generally Recognized As Safe. Under sections 201(s) and 409 of the Federal Food, Drug, and Cosmetic Act, any substance that is intentionally added to food is a food additive, that is subject to premarket review and approval by FDA, unless the substance is generally recognized, among qualified experts, as having been adequately shown to be safe under the conditions of its intended use, or unless the use of the substance is otherwise excepted from the definition of a food additive. For example, the GRAS compound can be a naturally occurring compound. For example, the GRAS compound can be selected from a food or food additive. In one embodiment, the GRAS compound is a vitamin, phenolic flavoring agent, natural oil, alcohol, amino acid or antioxidant. In one embodiment, the GRAS compound is a plant extract. In one embodiment, the GRAS compound is a plant substance primarily used for flavoring, coloring or preserving food. In one embodiment, the GRAS compound is an aliphatic or aromatic terpene hydrocarbon or a terpenoid.

In one embodiment, said substrate is not a VOC and its metabolite is not a VOC. In that embodiment, the substrate is a labelled reactant and labelled reactant and/or labelled metabolite can be measured in breath. The label may be an isotope label, for example 12C, 13C, 14C, 2H, 14N or 18O.

In a preferred embodiment, the substrate and/or metabolite is a VOC and the substrate is not labelled. Therefore, no labelling is required as the substrate and/or metabolite can be measured in breath without the use of any labels.

In one embodiment, the cancer is selected from lung cancer, breast cancer, ovarian cancer, bowel cancer, prostate cancer, bladder cancer, colorectal cancer, pancreas carcinoma, kidney cancer, renal cancer, leukaemias, multiple myeloma, lymphomas (e.g. Hodgkin's disease and non-Hodgkin's Lymphoma), brain cancer and other CNS and intracranial tumours cancer, head and neck cancer, oesophageal cancers, solid tumors such as sarcoma and carcinomas, mesothelioma, osteosarcoma, endometrial cancer or melanoma.

Exemplary types of lung cancer suitable for detection using the methods, system and kit described herein include, but are not limited to, small cell lung cancer (SCLC), non-small cell lung cancer (NSCLC), which includes squamous cell carcinoma, and adenocarcinoma. Other subtypes of lung cancer include bronchioloalveolar carcinoma, large cell carcinoma, carcinoid, adenoid cystic carcinoma, cylindroma, and mucoepidermoid carcinoma. In one embodiment, lung cancers are staged according to stages I-IV, with I being an early stage and IV being the most advanced. The methods of the invention would be of particular benefit to patients with surgically resected stage I or II non-squamous NSCLC. The current standard of care for most stage I non-squamous NSCLC is lobectomy and mediastinal lymph node dissection, without adjuvant chemotherapy. Better identification of good prognosis patient subsets might allow lesser surgical procedures to be employed with equal survival potential. Conversely, stage I subsets with a poor prognosis could be selected for treatment with adjuvant chemotherapy to reduce the risk of distant recurrence using current standard-of-care agents. Furthermore, patients identified to have a poor prognosis might also be considered for inclusion into clinical trials testing novel approaches and new therapeutic agents. Considering the current limitations of chemotherapy in stage I disease, a bioassay that is both prognostic and predictive of chemotherapy benefit would be especially beneficial. Lastly, stage I non-squamous NSCLC is likely to be of increasing importance in the future.

Patients with stage II NSCLC are currently recommended to undergo adjuvant chemotherapy after attempt at curative resection. The documented benefit of chemotherapy for these patients in terms of absolute improvement in 5-year survival, however, is small. As a result, many patients forego chemotherapy, particularly as they recover from their attempt at curative surgery. A diagnostic method that can better assign risk of recurrence to stage II patients may therefore improve compliance with current standard-of-care recommendations for adjuvant therapy in patients found to be at higher risk of recurrence. In a controlled, experimental setting, therapy may even be withheld from patients found to be at the lowest risk for recurrence even in stage II.

In one embodiment, the cancer is lung cancer and the enzyme is a lung cancer specific enzyme, that is an enzyme whose expression or activity is up- or downregulated in lung cancer tissue compared to healthy tissue. In one embodiment, the method includes the step of selecting a cancer-specific enzyme of interest and selecting a test substrate which is metabolised by said cancer-specific enzyme as discussed herein.

For example, as explained elsewhere, the expression of AKRs is upregulated in lung cancer tissue compared to healthy lung tissue. Thus, the concentration of a substrate of AKRs, that is an exogenous substrate, and/or its metabolite produced by the enzymatic conversion of the substrate by AKRs, can be measured in exhaled breath of a subject to detect the presence or absence of lung cancer or to assess progression of lung cancer.

Thus, in one embodiment of the methods described herein, the cancer is lung cancer and the lung cancer-specific enzyme is an AKR. In one embodiment, the AKR is selected from AKR1B10 or AKR1B15. In one embodiment, the substrate for the AKR, for example AKR1B10 or AKR1B15, is an aldehyde, ketone or other molecule. In one embodiment, the substrate is selected from cinnamaldehyde, citral or pyridine-3-aldehyde. In one embodiment, the substrate is cinnamaldehyde. Cinnamaldehyde is metabolised to cinnamyl alcohol by the AKR.

In one embodiment, the enzyme is an AKR, for example selected from AKR1B10 or AKR1B15, and the substrate is labelled, for example labelled retinaldehyde. In another embodiment, the substrate is labelled glucose.

In one embodiment, the methods of the invention comprise collecting a breath sample. The breath sample can include air exhaled from one or more different parts of the subject's body (e.g. nostrils, pharynx, trachea, bronchioles, alveoli etc.). For the collection of a breath sample and methods of measurement, the device and methods described in WO2017/187120 or WO2017/187141 (both publications are hereby incorporated by reference) can be used.

The methods involve determining the concentration of the substrate and/or metabolite in the breath sample and then comparing the concentration to a baseline value or range. Typically, the baseline value is representative of I concentration of the substrate and/or metabolite in a healthy person not suffering from, or destined to develop cancer, e.g. lung cancer. Variation of levels of substrate and/or metabolite from the baseline range (either up or down) indicates that the patient has an increased risk of long term mortality. For example, in embodiments where the enzyme is an AKR, an increased concentration of the metabolite in exhaled breath compared to a baseline value in a healthy individual indicates a risk of lung cancer. Conversely, a decreased level of the substrate in exhaled breath indicates a risk of lung cancer.

The algorithm used to calculate a risk assessment score in a method disclosed herein may group the concentration values of the substrate and/or metabolite, and the risk score can be derived from any algorithm known in the art. The algorithms are sets of rules for describing the risk assessment of cancer, e.g. lung cancer using expression of the panel of genes described herein. The rule set may be defined exclusively algebraically but may also include alternative or multiple decision points requiring domain-specific knowledge, expert interpretation or other clinical indicators. Many algorithms that can provide different risk assessments can be developed using concentration profiles of a suitable substrate and/or metabolite. For example, the risk scores of an individual may be generated using a Cox proportional hazard model. An individual's prognostic categorization can also be determined by using a statistical model or a machine learning algorithm, which computes the probability of recurrence based on the individual's concentration of the substrate and/or metabolite.

Based on the determination of a risk, individuals can be partitioned into risk groups (e.g., tertiles or quartiles) based on a selected value of the risk score, where all individuals with values in a given range can be classified as belonging to a particular risk group. Thus, the values chosen will define risk groups of patients with respectively greater or lesser risk. Risk groups can further be classified on different ranges of mortality, for example, on 6 month, 1-year, 2-year, 3-year, 4-year, 5-year, 10-year, 25-year mortality. Risk groups can further be classified on different ranges of events associated with lung cancer, which can include, but is not limited, likelihood of metastasis, recurrence, etc.

The concentration of the substrate and/or metabolite can be measured using methods known in the art. The concentration as used herein means the content or mass of the substrate and/or metabolite in exhaled breath as expressed, for example in grams/litre (g/l). In one embodiment, concentration is measured over time, for example by measuring the kinetics of the clearance. For example, concentration is measured by assessing the kinetic profile of the clearance of the substrate from breath which is then used as a readout. In addition or alternatively, secretion of metabolic products that can derive from the substrate can be measured over time. For example, clearance of the substrate from breath and secretion of metabolic products can both be measured in the same breath sample at the same time or at different times.

In one embodiment, the concentration or amount of the substrate and/or its metabolite may be determined in absolute or relative terms in multiple breath samples, e.g. in a first breath sample (collected at a first time period) and in a second and/or further breath sample (collected at a later, second or further time period), thus permitting analysis of the kinetics or rate of change of concentration thereof over time.

In one embodiment, the methods of the invention further comprise establishing a test subject value for one or more substrate and/or metabolite concentration.

In one embodiment, the methods of the invention further comprise comparing the test subject value to one or more reference value. In one embodiment, said reference value is from healthy subjects. In another embodiment, the reference value is from subjects diagnosed with cancer.

In one embodiment, the reference value is a healthy subject value corresponding to values calculated from healthy subjects. In one embodiment, the presence of one or more subject values at quantities greater than their respective range of healthy subject values indicates a substantial likelihood of a cancer disease state in the test subject.

In one embodiment, when an appropriate reference is indicative of a subject being free of cancer, e.g. lung cancer, a detectable difference (e.g., a statistically significant difference) between the value determined from a subject in need of characterization or diagnosis of cancer and the appropriate reference may be indicative of cancer in the subject. In one embodiment, when an appropriate reference is indicative of cancer, e.g. lung cancer, a lack of a detectable difference (e.g., lack of a statistically significant difference) between the value determined from a subject in need of characterization or diagnosis of cancer and the appropriate reference may be indicative of cancer or absence of cancer in the subject.

Thus, in one aspect, the methods include detecting the concentration of the substrate and/or metabolite in exhaled breath from the subject, and diagnosing the subject as having a likelihood or increased risk of a cancer disease state if the level of one or more of the substrate and/or metabolite is different from the healthy reference subject value.

Thus, the methods may further comprise the steps of:
a) Comparing the amount of one or more VOC in exhaled breath with a reference value, said reference value representing a known diagnosis, prognosis and/or monitoring status of a cancer; e.g. lung cancer;
b) Finding a deviation or no deviation of the amount of said one or more VOC from said reference value; and
c) Attributing said finding of deviation or no deviation to a particular diagnosis, prognosis and/or monitoring status of cancer, such as lung cancer, in the subject.

The term "deviation of the amount" refers either to elevated or reduced amounts of one or more VOC in a sample of exhaled breath from a subject compared to a reference value. By "elevated amounts" we mean that the amount of said one or more VOCS in a sample of exhaled breath from a subject is statistically higher than the reference value. By "reduced amounts" we mean that the amount of said one or more VOC in a sample of exhaled breath from a subject is statistically lower than the reference value. The amount may be considered to be statistically higher or lower if its value differs from a predetermined threshold value. This threshold value can, for example, be the median of the amount of VOC determined in a sample of exhaled breath from a population of healthy subjects.

The term "no deviation of the amount" refers to similar or unchanged amounts of one or more VOC of the invention in a sample of exhaled breath from a subject compared to a reference value. By "similar or unchanged level" is meant that the difference of the amount of said one or more VOC in a sample of exhaled breath from the subject compared to the reference value is not statistically significant. Preferably, the reference value is obtained in samples of exhaled breath obtained from one or more subjects of the same species and the same sex and age group as the subject in which the cancer is to be determined, prognosed or monitored. Alternatively, the reference value may be a previous value for the amount of one or more VOCS obtained in a sample of exhaled breath from a specific subject. This kind of reference value may be used if the method is to be used for monitoring the cancer, e.g. over time, or to monitor the response of a subject to a particular treatment.

The method may also comprise determining a risk score of the subject based on the concentration of the metabolite and/or substrate in the sample and using the risk score to provide a prognosis for the subject, wherein the risk score is indicative of said prognosis.

A sample of exhaled breath may be obtained by collecting exhaled air from the subject, for example by requesting the subject to exhale air into a gas-sampling container, such as a bag, a bottle or any other suitable gas-sampling product. Preferably the gas-sampling container resists gas permeation both into and out of the bag and/or is chemically inert, thereby assuring sample integrity. Exhaled breath may also be collected using a breath collector apparatus. Preferably, collection of a sample of exhaled breath is performed in a minimally invasive or a non-invasive manner.

The determination of the amount of one or more VOCS in a sample of exhaled breath from a subject may be performed by the use of at least one technique including, but not limited to, Gas-Chromatography (GC), Gas-Chromatography-lined Mass Spectrometry (GC/MS), Liquid Chromatography-tandem mass spectrometry (LC/MS), Ion Mobility Spectrometry/Mass Spectrometry (IMS/MS), Proton Transfer Reaction Mass-Spectrometry (PTR-MS), Electronic Nose device, quartz crystal microbalance or chemically sensitive sensors.

The amount of one or more VOCs in a sample of exhaled breath from a subject may be determined using thermal desorption-gas chromatography-time of flight-mass spectrometry (GC-fof-MS). In certain embodiments, breath of the subject is collected in an inert bag, then the content of the bag is transported under standardised conditions onto desorption tubes and VOCs are analyzed by thermally desorbing the content of the tube and then separated by capillary gas chromatography. Then volatile organic peaks are detected with MS and identified using for example a library, such as the National Institute of Standards and Technology. Thermal desorption may be performed at the GC inlet at a temperature of, e.g., about 200-350° C. In all chromatography, separation occurs when the sample mixture is introduced (injected) into a mobile phase. Gas chromatography (GC) typically uses an inert gas such as helium as the mobile phase. GC/MS allows for the separation, identification and/or quantification of individual components from a biological sample. MS methods which may be used with the present invention include, but are not limited to, electron ionization, electrospray ionization, glow discharge, field desorption (FD), fast atom bombardment (FAB), thermospray, desorption/ionization on silicon (DIOS), Direct Analysis in Real Time (DART), atmospheric pressure chemical ionization (APCI), secondary ion mass spectrometry (SIMS), spark ionization and thermal ionization (TIMS). Matrix assisted laser desorption ionization time-of-flight mass spectrometry (MALDI-TOF-MS) is an example of a mass spectroscopy method which may be used to determine one or more VOCs from a sample of exhaled breath from a subject.

In one embodiment, the method comprises collecting different selected exhaled breath samples, or fractions thereof, on a single breath sample capture device, the method comprising the steps of:
  (a) collecting a first exhaled breath sample by contacting the sample with a capture device comprising an adsorbent material;
  (b) collecting a second exhaled breath sample by contacting the second sample with said capture device, wherein the first and second exhaled breath samples are caused to be captured on the capture device in a spatially separated manner.

In some embodiments, the capture device comprises an adsorbent material in the form of a porous polymeric resin. Suitable adsorbent materials include Tenax® resins and Carbograph® materials. Tenax® is a porous polymeric resin based on a 2,6-diphenyl-p-propylene oxide monomer. Carbograph® materials are graphitized carbon blacks. In one embodiment, the material is Tenax GR, which comprises a mixture of Tenax® TA and 30% graphite. One Carbograph® adsorbent is Carbograph STD. In one embodiment, the capture device comprises both Tenax GR and Carbograph STD. The capture device is conveniently a sorbent tube. These are hollow metal cylinders, typically of standard dimensions (3½ inches in length with a ¼ inch internal diameter) packed with a suitable adsorbent material.

The methods of the invention may further include the step of selecting a treatment for said cancer following the diagnosis. This treatment refers to anti-cancer therapy, for example chemotherapy, radiotherapy, surgery or antibody therapy. The methods may then further include administering said treatment to said subject.

The methods of the invention may further include the initial step of identifying or selecting an enzyme that is cancer-specific.

The invention also relates to a method for monitoring the progression of cancer, such as lung cancer, in a subject diagnosed with cancer comprising assessing the activity of a cancer-specific enzyme by measuring the concentration of an exogenous substrate for said enzyme and/or measuring the concentration of a metabolite for said substrate in exhaled breath of the subject.

In one embodiment, the subject has undergone treatment. This treatment refers to anti-cancer therapy, for example chemotherapy, radiotherapy, surgery or antibody therapy.

The invention also relates to a method for determining efficacy of a treatment in a subject diagnosed with cancer such as lung cancer, comprising assessing the activity of a cancer-specific enzyme, such as an AKR enzyme, by measuring the concentration of an exogenous substrate for said enzyme and/or measuring the concentration of a metabolite of said substrate in exhaled breath of the subject wherein said subject has received anti-cancer treatment.

The invention also relates to a method of treating a subject having a cancer, such as lung cancer, the method comprising a method as described herein, e.g. assessing the activity of a cancer-specific enzyme, such as an AKR enzyme, by measuring the concentration of an exogenous substrate for said enzyme and/or measuring the concentration of a metabolite of said substrate in exhaled breath of a subject. The method may also comprise determining a risk score of the subject based on the concentration of the metabolite and/or substrate in the sample; using the risk score to provide a prognosis for the subject, wherein the risk score is indicative of said prognosis and wherein the prognosis provides a low risk assessment or a high risk assessment; and treating the subject having a high risk assessment with a therapeutic therapy, e.g. chemotherapy or surgery.

The invention also relates to the use of a VOC in a method described herein.

The invention also relates to an in vitro method for identifying a VOC for use in a method described herein comprising exposing a cancer-specific enzyme or cancer tissue to a test VOC and measuring the metabolism of the VOC to assess specificity and activity of the enzyme for the test VOC. In one embodiment, the method uses a library approach and an array of compounds is screened. Standard enzyme assays can be used to measure metabolism.

The invention also relates to a system for the detection of cancer comprising assessing the activity of an enzyme that is differentially expressed in cancer tissue by measuring the concentration of an exogenous substrate for said enzyme and/or measuring the concentration of a metabolite for said substrate in exhaled breath of a subject wherein said system comprises a device for capturing a breath sample from a patient.

In one embodiment, the system includes a device for capturing a breath sample as described in WO2017/187120 or WO2017/187141. The device in WO2017/187120 comprises a mask portion which, in use, is positioned over a subject's mouth and nose, so as to capture breath exhaled from the subject. The exhaled breath samples are fed into tubes containing a sorbent material, to which the compounds of interest adsorb. After sufficient sample has been obtained, the sorbent tubes are removed from the sampling device and the adsorbed compounds desorbed (typically by heating) and subjected to analysis to identify the presence and/or amount of any particular compounds or other substances of interest. The preferred analytic technique is field asymmetric ion mobility spectroscopy (abbreviated as "FAIMS"). The method in WO2017/187141 refinement of the method described in WO2017/187120 is disclosed in WO2017/187141. In that document, it is taught to use breath sampling apparatus substantially of the sort described in WO2017/187120, but in a way such as to selectively sample desired portions of a subject's exhaled breath, the rationale being that certain biomarkers or other analytes of interest are relatively enriched in one or more fractions of the exhaled breath, which fractions themselves are relatively enriched in air exhaled from different parts of the subject's body (e.g. nostrils, pharynx, trachea, bronchioles, alveoli etc).

The invention also relates to a device for use in the methods described herein.

The invention also relates to a kit comprising a system for the detection of cancer comprising assessing the activity of an enzyme that is differentially expressed in cancer tissue, e.g. and AKR enzyme, by measuring the concentration of an exogenous substrate for said enzyme and/or measuring the concentration of a metabolite for said substrate in exhaled breath of a subject wherein said system comprises a device for capturing a breath sample from a patient.

The kit as described herein may includes a composition for administration that comprises the substrate. This can be for administration as described above. It may also include a pharmaceutically acceptable carrier or vehicle. This can be a particulate, so that the compositions are, for example, in tablet or powder form. The term "carrier" refers to a diluent, adjuvant or excipient, with which a substrate is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. The composition can be in the form of a liquid, e.g., a solution, emulsion or suspension. The liquid can be useful for delivery by injection, infusion (e.g., IV infusion) or sub-cutaneously. As a solid composition for oral administration, the composition can be formulated into a powder, granule, compressed tablet, pill, capsule, chewing gum, wafer or the like form. Compositions can take the form of one or more dosage units.

Typically, the amount of the substrate administered as part of the methods of the invention or the amount of the substrate included in the composition comprised in the kit is at least about 0.01% of the substrate by weight of the composition. When intended for oral administration, this amount can be varied to range from about 0.1% to about 80% by weight of the composition. For administration by injection, the composition can comprise from about typically about 0.1 mg/kg to about 250 mg/kg of the subjects body weight, preferably, between about 0.1 mg/kg and about 20 mg/kg of the subjects body weight, and more preferably from about 1 mg/kg to about 10 mg/kg of the subjects body weight.

The invention also relates to the use of a substance, i.e. an exogenous substance that is not produced by the human body, e.g. a GRAS substance, e.g. cinnamaldehyde, citral or pyridine-3-aldehyde in a method described herein. In one embodiment, the substance is not labelled. Thus, the invention also relates to the use of a substance that is not produced by a human body in a method for the detection or prognosis of cancer comprising assessing the activity of a cancer specific enzyme, e.g. an aldo-keto reductase (AKR) by measuring the concentration of an exogenous substrate for said enzyme and/or measuring the concentration of a metabolite of said substrate in exhaled breath of a subject.

Unless otherwise defined herein, scientific and technical terms used in connection with the present disclosure shall have the meanings that are commonly understood by those of ordinary skill in the art. While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification are incorporated herein by reference in their entirety.

"and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein. Unless context dictates otherwise, the descriptions and definitions of the features set out above are not limited to any particular aspect or embodiment of the invention and apply equally to all aspects and embodiments which are described.

EXAMPLES

The invention is further described in the following non-limiting examples.

Example 1

To confirm that AKR1B10 expression is increased in lung cancer compared to normal lung, the inventors analysed independent datasets of lung adenocarcinoma (LUAD) and lung squamous carcinoma (LUSC) that AKR1B10 is indeed activated, at the mRNA level, in cancer vs normal tissue (FIG. 1A). The inventors also found that the expression of another AKR isoform was increased both lung cancer types, namely AKR1B15. AKR1B15 shows 92% homology with AKR1B10, as well as similar substrate specificities (Giménez-Dejoz, 2015). Together with evidence reported in the literature, these findings suggest that both AKR1B10 and AKR1B15 are activated in lung cancer cells as a mechanism to counteract lipid peroxidation. Of note, AKR1B10 is normally expressed in the gastrointestinal tract, while AKR1B15 is found expressed in female reproductive organs (https://www.proteinatlas.org/) and neither enzyme is expressed in normal lung. This finding suggests that AKR1B10-B15 represents lung cancer-specific metabolic activities that, being absent in the surrounding normal lung tissue, indicate the presence of lung cancer.

Example 2

Cinnamaldehyde and Cinnamyl alcohol standards can be measured. What was observed was a washout of chemicals originating as standards injected into the analysis system. This is shown in FIG. 3. The experiment used standards to test the hardware used. This demonstrates that analytical methods exist to determine the concentration of these substances. TD-GC-MS(TOF) instrumentation used for this experiment includes a BenchTOF HD, Agilent GC 7890B and a Markes TD-100xr.

Example 3

The work flow of the detection method is shown in FIG. 2.

An exogenous substance, e.g. Cinnamaldehyde, is given in a known quantity to a subject, for example by diluting approximately 750 mg Cinnamon extract powder in 50 ml water (substrate administration step). This liquid is then ingested by the test subject.

After a predetermined time, such as 1 to 24 hours, a breath sample is taken from the subject (breath sampling step). Alternatively, multiple breath samples are taken at defined time points. The concentration of the exhaled substrate, e.g. Cinnamaldehyde and/or the exhaled metabolite, e.g. Cinnamyl alcohol, in breath is measured (referred to as substrate related VOCs in the figure), for example using TD-GC-MS (TOF) instrumentation (TD-GC-MS measurement step).

The above is carried out in a healthy subject, preferably a plurality of healthy subjects, to establish a reference value for a healthy subject. The above is also carried out in the test subject. The test subject value(s) obtained are then compared to the threshold from a healthy subject that does not have cancer.

Based on this comparison, a risk score is determined, using standard algorithms and statistical analysis (statistical analysis step). On that basis, a disease diagnosis or prognosis can be made (not shown in the figure).

Depending on the diagnosis, a treatment is administered (not shown in the figure).

BIBLIOGRAPHY

Alvarez, Samantha W., Vladislav O. Sviderskiy, Erdem M. Terzi, Thales Papagiannakopoulos, Andre L. Moreira, Sylvia Adams, David M. Sabatini, Kivanç Birsoy, and Richard Possemato. 2017. "NFS1 Undergoes Positive Selection in Lung Tumours and Protects Cells from Ferroptosis." Nature 551 (7682): 639. https://doi.org/10.1038/nature24637.

Ayala, Antonio, Mario F Munoz, and Sandro Argüelles. 2014. "Lipid Peroxidation: Production, Metabolism, and Signaling Mechanisms of Malondialdehyde and 4-Hydroxy-2-Nonenal." Oxidative Medicine and Cellular Longevity 2014: 360438. https://doi.org/10.1155/2014/360438.

Bachur, N. 1976. "Cytoplasmic Aldo-Keto Reductases: A Class of Drug Metabolizing Enzymes." Science 193 (4253): 595-97. https://doi.org/10.1126/science.959821.

Barski, Oleg A, Srinivas M Tipparaju, and Aruni Bhatnagar. 2008. "The Aldo-Keto Reductase Superfamily and Its Role in Drug Metabolism and Detoxification." Drug Metabolism Reviews 40 (4): 553-624. https://doi.org/10.1080/03602530802431439.

Cao, Deliang, Sheung Tat Fan, and Stephen S. M. Chung. 1998. "Identification and Characterization of a Novel Human Aldose Reductase-like Gene." Journal of Biological Chemistry 273 (19): 11429-35. https://doi.org/10.1074/jbc.273.19.11429.

DeNicola, Gina M, Florian A Karreth, Timothy J Humpton, Aarthi Gopinathan, Cong Wei, Kristopher Frese, Dipti Mangal, et al. 2011. "Oncogene-Induced Nrf2 Transcription Promotes ROS Detoxification and Tumorigenesis." Nature 475 (7354): 106-9. https://doi.org/10.1038/nature10189.

Dixon, Scott J, Darpan N Patel, Matthew Welsch, Rachid Skouta, Eric D Lee, Miki Hayano, Ajit G Thomas, et al. 2014. "Pharmacological Inhibition of Cystine-Glutamate Exchange Induces Endoplasmic Reticulum Stress and Ferroptosis." ELife 3 (May): e02523. https://doi.org/10.7554/eLife.02523.

Fan, Teresa W M, Andrew N Lane, Richard M Higashi, Mohamed A Farag, Hong Gao, Michael Bousamra, and Donald M Miller. 2009. "Altered Regulation of Metabolic Pathways in Human Lung Cancer Discerned by 13C Stable Isotope-Resolved Metabolomics (SIRM)." Molecular Cancer 8 (1): 41. https://doi.org/10.1186/1476-4598-8-41.

Faubert, Brandon, Kevin Y. Li, Ling Cai, Christopher T. Hensley, Jiyeon Kim, Lauren G. Zacharias, Chendong Yang, et al. 2017. "Lactate Metabolism in Human Lung Tumors." Cell 171 (2): 358-371. e9. https://doi.org/10.1016/J.CELL.2017.09.019.

Fukumoto, S.-i. 2005. "Overexpression of the Aldo-Keto Reductase Family Protein AKR1B10 Is Highly Correlated with Smokers' Non-Small Cell Lung Carcinomas." Clinical Cancer Research 11 (5): 1776-85. https://doi.org/10.1158/1078-0432.CCR-04-1238.

Gaude, Edoardo, and Christian Frezza. 2016. "Tissue-Specific and Convergent Metabolic Transformation of Cancer Correlates with Metastatic Potential and Patient Survival." Nature Communications 7 (October): 13041. https://doi.org/10.1038/ncomms13041.

Giménez-Dejoz, Joan, Michal H. Kolar, Francesc X. Ruiz, Isidro Crespo, Alexandra Cousido-Siah, Alberto Podjarny, Oleg A. Barski, et al. 2015. "Substrate Specificity, Inhibitor Selectivity and Structure-Function Relationships of Aldo-Keto Reductase 1B15: A Novel Human Retinaldehyde Reductase." Edited by Fernando Rodrigues-Lima. PLOS ONE 10 (7): e0134506. https://doi.org/10.1371/journal.pone.0134506.

Grimshaw, Charles E. 1992. "Aldose Reductase: Model for a New Paradigm of Enzymic Perfection in Detoxification Catalysts." Biochemistry 31 (42): 10139-45. https://doi.org/10.1021/bi00157a001.

Hensley, Christopher T, Brandon Faubert, Qing Yuan, Naama Lev-Cohain, Eunsook Jin, Jiyeon Kim, Lei Jiang, et al. 2016. "Metabolic Heterogeneity in Human Lung Tumors." Cell 164 (4): 681-94. https://doi.org/10.1016/j.cell.2015.12.034.

Jin, Junfei, Weijia Liao, Wenmin Yao, Rongping Zhu, Yulan Li, and Songqing He. 2016. "Aldo-Keto Reductase Family 1 Member B 10 Mediates Liver Cancer Cell Proliferation through Sphingosine-1-Phosphate." Scientific Reports 6 (February): 1-11. https://doi.org/10.1038/srep22746.

MacLeod, A Kenneth, Lourdes Acosta-Jimenez, Philip J Coates, Michael McMahon, Frank A Carey, Tadashi Honda, Colin J Henderson, and C Roland Wolf. 2016. "Aldo-Keto Reductases Are Biomarkers of NRF2 Activity and Are Co-Ordinately Overexpressed in Non-Small Cell Lung Cancer." British Journal of Cancer 115 (12): 1530-39. https://doi.org/10.1038/bjc.2016.363.

Martin, Hans-Jörg, and Edmund Maser. 2009. "Role of Human Aldo-Keto-Reductase AKR1B10 in the Protection against Toxic Aldehydes." Chemico-Biological Interactions 178 (1-3): 145-50. https://doi.org/10.1016/J.CBI.2008.10.021.

Mochalski, Pawef, Andreas Sponring, Julian King, Karl Unterkofler, Jakob Troppmair, and Anton Amann. 2013. "Release and Uptake of Volatile Organic Compounds by Human Hepatocellular Carcinoma Cells (HepG2) in Vitro." Cancer Cell International 13 (1): 72. https://doi.org/10.1186/1475-2867-13-72.

Nishinaka, Toru, Takeshi Miura, Kahori Shimizu, and Tomoyuki Terada. 2017. "Identification and Characterization of Functional Antioxidant Response Elements in the Promoter of the Aldo-Keto Reductase AKR1B10 Gene." Chemico-Biological Interactions 276 (October): 160-66. https://doi.org/10.1016/j.cbi.2017.02.008.

Pavlova, Natalya N., and Craig B. Thompson. 2016. "The Emerging Hallmarks of Cancer Metabolism." Cell Metabolism 23 (1): 27-47. https://doi.org/10.1016/j.cmet.2015.12.006.

Petrash, J Mark, Theresa M Harter, Catherine S Devine, Peter O Olins, Aruni Bhatnagar, Siqi Liu, and Satish K Srivastava. 1992. "Involvement of Cysteine Residues in Catalysis and Inhibition of Human Aldose Reductase." The Journal of Biological Chemistry 267 (34): 24833-40.

Reznik, Ed, Martin L Miller, Yasin Ş enbabaoğlu, Nadeem Riaz, Judy Sarungbam, Satish K Tickoo, Hikmat A Al-Ahmadie, et al. 2016. "Mitochondrial DNA Copy Number Variation across Human Cancers." ELife 5 (February): e10769. https://doi.org/10.7554/eLife.10769.

Ross, Brian, Stephanie Puukila, Imran Malik, Slim Babay, Maurice Lecours, Adrian Agostino, Taddese Wondimu, and Neelam Khaper. 2013. "The Use of SIFT-MS to Investigate Headspace Aldehydes as Markers of Lipid Peroxidation." Current Analytical Chemistry 9 (4): 600-613. https://doi.org/10.2174/15734110113099990025.

Schallschmidt, Kristin, Roland Becker, Christian Jung, Jana Rolff, Iduna Fichtner, and Irene Nehls. 2015. "Investigation of Cell Culture Volatilomes Using Solid Phase Micro Extraction: Options and Pitfalls Exemplified with Adenocarcinoma Cell Lines." Journal of Chromatography B 1006 (December): 158-66. https://doi.org/10.1016/j.jchromb.2015.10.004.

Sellers, Katherine, Matthew P. Fox, Michael Bousamra, Stephen P. Slone, Richard M. Higashi, Donald M. Miller, Yali Wang, et al. 2015. "Pyruvate Carboxylase Is Critical for Non-Small-Cell Lung Cancer Proliferation." The Journal of Clinical Investigation 125 (2): 687-98. https://doi.org/10.1172/JCI72873.

Singh, Anju, Vikas Misra, Rajesh K Thimmulappa, Hannah Lee, Stephen Ames, Mohammad 0 Hogue, James G Herman, et al. 2006. "Dysfunctional KEAP1-NRF2 Interaction in Non-Small-Cell Lung Cancer." Edited by Matthew Meyerson. PLoS Medicine 3 (10): e420. https://doi.org/10.1371/journal.pmed.0030420.

Srivastava, Sanjay, Matthew Spite, John O. Trent, Matthew B. West, Yonis Ahmed, and Aruni Bhatnagar. 2004. "Aldose Reductase-Catalyzed Reduction of Aldehyde Phospholipids." Journal of Biological Chemistry 279 (51): 53395-406. https://doi.org/10.1074/jbc.M403416200.

Stockwell, Brent R., Jose Pedro Friedmann Angeli, Hülya Bayir, Ashley I. Bush, Marcus Conrad, Scott J. Dixon, Simone Fulda, et al. 2017. "Ferroptosis: A Regulated Cell Death Nexus Linking Metabolism, Redox Biology, and Disease." Cell 171 (2): 273-85. https://doi.org/10.1016/J.CELL.2017.09.021.

Tong, Ying-Hui, Bo Zhang, Yun Fan, and Neng-Ming Lin. 2015. "Keap1-Nrf2 Pathway: A Promising Target towards Lung Cancer Prevention and Therapeutics." Chronic Diseases and Translational Medicine 1 (3): 175-86. https://doi.org/10.1016/J.CDTM.2015.09.002.

Yan, Ruilan, Xuyu Zu, Jun Ma, Ziwen Liu, Moses Adeyanju, and Deliang Cao. 2007. "Aldo-Keto Reductase Family 1 B10 Gene Silencing Results in Growth Inhibition of Colorectal Cancer Cells: Implication for Cancer Intervention." International Journal of Cancer 121 (10): 2301-6. https://doi.org/10.1002/ijc.22933.

Yin, Huiyong, Libin Xu, and Ned A Porter. 2011. "Free Radical Lipid Peroxidation: Mechanisms and Analysis." Chemical Reviews 111 (10): 5944-72. https://doi.org/10.1021/cr200084z.

Yoshitake, H., M. Takahashi, H. Ishikawa, M. Nojima, H. Iwanari, A. Watanabe, H. Aburatani, et al. 2007. "Aldo-Keto Reductase Family 1, Member B10 in Uterine Carcinomas: A Potential Risk Factor of Recurrence after Surgical Therapy in Cervical Cancer." International Journal of Gynecologic Cancer 17 (6): 1300-1306. https://doi.org/10.1111/j.1525-1438.2007.00932.x.

Zhao, Dongxin, Mehmet G. Badur, Jens Luebeck, Jose H. Magana, Amanda Birmingham, Roman Sasik, Christopher S. Ahn, Trey Ideker, Christian M. Metallo, and Prashant Mali. 2018. "Combinatorial CRISPR-Cas9 Metabolic Screens Reveal Critical Redox Control Points Dependent on the KEAP1-NRF2 Regulatory Axis." Molecular Cell 69 (4): 699-708.e7. https://doi.org/10.1016/j.molcel.2018.01.017.

Zhou, Zhen, Yi Zhao, Lingping Gu, Xiaoming Niu, and Shun Lu. 2018. "Inhibiting Proliferation and Migration of Lung Cancer Using Small Interfering RNA Targeting on Aldo-Keto Reductase Family 1 Member B10." Molecular Medicine Reports 17 (2): 2153-60. https://doi.org/10.3892/mmr.2017.8173.

The invention claimed is:

1. A method for the detection or prognosis of cancer comprising assessing the activity of an aldo-keto reductase (AKR) by measuring the concentration of an exogenous substrate for said AKR and/or measuring the concentration of a metabolite of said substrate in exhaled breath of a subject, wherein the cancer is lung cancer and where in said AKR is AKR1B10 or AKR1B15.

2. The method according to claim 1 wherein the substrate and/or its metabolite is a volatile organic compound (VOC).

3. The method according to claim 1 wherein the substrate is a generally recognized as safe (GRAS) compound.

4. The method according to claim 1 wherein the substrate is labelled.

5. The method according to claim 1 wherein said lung cancer is selected from small cell lung cancer, non-small cell lung cancer, squamous cell carcinoma or adenocarcinoma.

6. The method according to claim 1 wherein the substrate is labelled retinaldehyde.

7. The method according to claim 6 wherein said label is 12C, 13C, 14C, 2H, 14N or 18O.

8. The method according to claim 1 wherein said substrate is cinnamaldehyde, citral or pyridine-3-aldehyde.

9. The method according to claim 1 wherein said method comprises establishing a test subject value based on a concentration of said substrate or metabolite.

10. The method according to claim 9 wherein said test subject value is compared to one or more reference value and wherein a difference in the test subject value and a reference value indicates a likelihood of cancer.

11. The method according to claim 10 wherein said reference value is the value of a subject that has been diagnosed with a cancer.

12. The method according to claim 11 wherein said reference value is the value of a subject who has not been diagnosed with cancer.

13. The method according to claim 1 wherein the concentration of more than one exogenous substrates and/or the concentration of more than one metabolites is measured.

14. The method according to claim 1 wherein the method comprises providing the substrate to the subject.

15. The method according to claim 1 wherein the method comprises collection of a breath sample from said subject.

16. The method according to claim 1 wherein the substrate is not labelled.

17. A method for monitoring the progression of cancer in a subject diagnosed with cancer comprising assessing the activity of an aldo-keto reductase (AKR) by measuring the concentration of an exogenous substrate for said AKR and/or measuring the concentration of a metabolite of said substrate in exhaled breath of the subject, wherein the cancer is lung cancer and wherein said AKR is AKR1B10 or AKR1B15.

18. The method according to claim 17 wherein the subject has undergone anti-cancer treatment.

19. A method for determining efficacy of a treatment comprising in a subject diagnosed with cancer assessing the activity of an aldo-keto reductase (AKR) by measuring the concentration of an exogenous substrate for said AKR and/or measuring the concentration of a metabolite of said substrate in exhaled breath of the subject wherein said subject has received anti-cancer treatment, wherein the cancer is lung cancer and wherein said AKR is AKR1B10 or AKR1B15.

20. A method of treating cancer in a subject comprising assessing the activity of an aldo-keto reductase (AKR) by measuring the concentration of an exogenous substrate for said AKR and/or measuring the concentration of a metabolite of said substrate in exhaled breath of the subject wherein said subject has received anti-cancer treatment, wherein the cancer is lung cancer and wherein said AKR is AKR1B10 or AKR1B15.

21. A system for the detection of cancer comprising assessing the activity of an aldo-keto reductase (AKR) by measuring the concentration of an exogenous substrate for said AKR and/or measuring the concentration of a metabolite of said substrate in exhaled breath of a subject wherein said system comprises a device for capturing a breath sample from the subject, wherein the cancer is lung cancer and wherein said AKR is AKR1B10 or AKR1B15.

22. A kit comprising a system according to claim 21.

* * * * *

UNITED STATES PATENT AND TRADEMARK OFFICE
CERTIFICATE OF CORRECTION

Page 1 of 1

PATENT NO. : 12,306,174 B2
APPLICATION NO. : 17/273294
DATED : May 20, 2025
INVENTOR(S) : Max Allsworth, Edoardo Gaude and Marc van der Schee It is certified that error appears in the above-identified patent and that said Letters Patent is hereby corrected as shown below:

In the Claims

In Claim 1, Column 22, Line 41, delete "and where in said" and insert -- and wherein said --.

Signed and Sealed this
Eighth Day of July, 2025

Coke Morgan Stewart
*Acting Director of the United States Patent and Trademark Office*